US006616927B2

(12) United States Patent
Hodgkinson et al.

(10) Patent No.: US 6,616,927 B2
(45) Date of Patent: *Sep. 9, 2003

(54) PROCESSES FOR PRODUCTION OF IMMUNOGLOBULIN A IN MILK

(75) Inventors: Alison Joy Hodgkinson, Hamilton (NZ); Steven Charles Hodgkinson, Hamilton (NZ)

(73) Assignee: Agresearch Limited, Hamilton (NZ)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/424,246

(22) PCT Filed: May 29, 1998

(86) PCT No.: PCT/NZ98/00070

§ 371 (c)(1),
(2), (4) Date: Feb. 29, 2000

(87) PCT Pub. No.: WO98/54226

PCT Pub. Date: Dec. 3, 1998

(65) Prior Publication Data

US 2002/0076410 A1 Jun. 20, 2002

(30) Foreign Application Priority Data

May 29, 1997 (NZ) .................................................. 314959

(51) Int. Cl.[7] .............................................. A61K 39/00
(52) U.S. Cl. .................................. 424/157.1; 424/184.1
(58) Field of Search ........................... 424/157.1, 184.1

(56) References Cited

U.S. PATENT DOCUMENTS

| 4,229,342 A | | 10/1980 | Mirabel ....................... 260/120 |
|---|---|---|---|
| 4,582,580 A | | 4/1986 | Goudal et al. ............ 204/182.6 |
| 4,644,056 A | | 2/1987 | Kothe et al. ................. 530/387 |
| 5,001,230 A | * | 3/1991 | Brown et al. |
| 5,013,824 A | * | 5/1991 | Abrams et al. |
| 5,066,491 A | | 11/1991 | Stott et al. ................... 424/85.8 |
| 5,155,213 A | * | 10/1992 | Padron |
| 5,260,057 A | | 11/1993 | Cordle et al. ............... 424/85.8 |
| 5,418,137 A | * | 5/1995 | Yamanaka et al. |
| 5,650,173 A | * | 7/1997 | Ramstack et al. |

FOREIGN PATENT DOCUMENTS

| EP | 0320152 | 6/1989 |
|---|---|---|
| EP | 0469359 | 2/1992 |
| GB | 1573995 | 9/1980 |
| GB | 2179947 | 3/1987 |
| NZ | 239466 | 8/1991 |
| WO | WO97/27757 | 8/1997 |

OTHER PUBLICATIONS

Am J Vet Res, vol. 45, No. 1, Saif et al, "Immune response of pregnant cows to bovine . . . ", pp. 49–58, Jan. 1984.
Vet Immunology & Immunopathology, vol. 6, Opdebeeck et al, "Comparative effect of selected . . . ", pp. 341–351, 1984.
Vaccine, vol. 11, Issue 2, Husband, "Novel vaccination strategies for the control . . . ", pp. 107–112, 1993.
Vaccines in Agriculture, Watson et al, "Immunological effector mechanisms in ruminants", pp. 21–36, 1994.
J Diary Sci, vol. 80, No. 10, Hogan et al, "Responses of antibody Titers to Itramammary . . . ", pp. 2398–2402, pgs. 1997.
Australian Jour of Dairy Tech, Sheldrake, "Immune mechanisms of the ruminant mammary gland", pp. 30–32, Mar./Jun. 1987.
Immunology, vol. 56, Sheldrake et al, "The effect of intra–peritoneal and intramammary . . . ", pp. 605–615, 1985.
Res in Vet Sci, vol. 38, Sheldrake et al, "Specific antibody–containing cells in the mammary . . . ", pp. 312–316, 1985.
Vaccine, vol. 3, Crouch, "Vaccination against enteric rota and coronaviruses in cattle . . . ", pp. 284–291, Sep. 1985.
Cambridge Univ. Press, "The mucosal immune system with particular reference to ruminant animals", pp. 429–457, 1986.
Res in Vet Science, vol. 45, Sheldrake et al, "Origin of antibody containing cells in the ovine . . . ", pp. 156–159, 1988.
Res inVet Science, vol. 49, Sheldrake et al, "IgA immune responses in the respiratory . . . ", pp. 98–103, 1990.
Health and Production for the 21st Century, Husband et al, "The development of vaccines to protect . . . ", pp. 82–88, 1993.
Eur. J. Pediatr., vol. 132, Mietens et al, "Treatment of Infantile *E. coli* gastroenteritis . . . ", pp. 239–252, 1979.
Ad. Exp. Med & Biol, Pahud et al, "Bovine milk antibodies in the treatment of enteric infections . . . ", pp. 591–600, 1981.
J of Inf. Diseases, vol. 156, No. 1, Hilpert et al, "Use of bovine milk concentrate containing . . . ", pp. 158–166, Jul. 1987.
J of Cli. Microbiology, vol. 25, No. 6, Brussow et al, "Bovine milk immunoglobulins for passive . . . ", pp. 982–986, Jun. 1987.

(List continued on next page.)

Primary Examiner—Patrick J. Nolan
(74) Attorney, Agent, or Firm—Jacobson Holman PLLC

(57) ABSTRACT

The present invention provides a process for production of immunoglobulin A in milk from hyperimmunised mammals, using a three-route immunisation protocol. Also provided is milk containing immunoglobulin A produced by the process of the invention. These products are useful in producing formulations for passive immunisation against the selected pathogens. These formulations are further useful for preparation of further processed products.

33 Claims, 10 Drawing Sheets

OTHER PUBLICATIONS

Antibodies: A Laboratory Manual, Chapter 5, "Intravenous injections", pp. 110–114, 1998 Harlow.

ILAR Journal, vol. 37, No. 3, Jackson et al, "Institutional policies and guidelines on adjuvants . . . ", pp. 141–152, 1995.

Agric. Biol. Chem., vol. 46, No. 6, Kanamaru et al, "Purification of Secretory IgA from Bovine . . . ", pp. 1531–1537, 1982.

Can J Vet Res, vol. 50, Nielsen "A method for preparation of IgA from Bovine Mammary Secretions", pp. 227–231, 1986.

Milchwissenschaft 48, vol. 5, Kanamaru et al, "Ultrafiltration and gel filtration methods for . . . ", pp. 247–251, 1993.

International Diary Federation, Ruiz, Jr., "Antibodies from milk for the prevention and . . . ", pp. 108–131, Aug. 31–Sep. 1, 1993.

The Lancet, Tzipori et al, Chronic cryptosporidial diarrhoea and hyperimmune cow colostrum, pp. 344–345, 1987 letter.

J of App Bacteriology, vol. 74, Husu et al, "Production of hyperimmune bovine colostrum . . . ", pp. 564–569, 1993.

J. Protozool, vol. 38, No. 6, Fayer et al, "Production and preparation of hyperimmune bovine . . . ", pp. 38S–39S, Nov.–Dec. 1991.

Am. J. Med. Hyg., vol. 47, No. 3, Tacket et al, "Efficacy of bovine milk immunoglobulin . . . ", pp. 276–283, 1992.

Inf and Immunity, vol. 55, No. 10, Michalek et al, "Protection of Gnotobiotic Rats against . . . ", pp. 2341–2347, Oct. 1987.

Gastroenterology, vol. 98, No. 2, Ingar et al, "Cessation of cryptosporidium–associated diarrhea . . . ", pp. 486–489, 1990.

J of British Pediatric Assoc., vol. 70, No. 4, Heaton, "Bovine colostrum immunoglobulin concnetrate . . . ", pp. 355–357, 1994 letter.

\* cited by examiner

PROCESSES FOR PRODUCTION OF IMMUNOGLOBULIN A IN MILK

The present application is a 35 U.S.C. 371 of PCT/NZ98/00070 filed May 29, 1998.

TECHNICAL FIELD

This invention relates to processes for producing immunoglobulin A in mammals, processes for producing milk containing immunoglobulin A and to the uses of the immunoglobulin A and milk produced.

BACKGROUND

Immunoglobulin A (IgA) is a well documented immunoglobulin present in almost all body fluids. It is thought to play a major role in the protection of the host from infection by pathogenic organisms invading via the mucosal surfaces of the respiratory, gastrointestinal and urogenital tracts. IgA participates in the clearance of pathogenic bacterial, viral or parasitical organisms and a variety of ingested or inhaled antigens from the mucosal surfaces by neutralising toxins and viral particles, inhibiting adherence of bacterial pathogens and preventing colonisation and penetration of mucosal surfaces by pathogenic microorganisms. The key role of immunoglobulins including IgA in milk therefore is to provide local protective immunity in the gastrointestinal tract of the offspring during the suckling period.

Immunoglobulins have come to be recognised as useful in the pharmaceutical and veterinary fields for treating bacterial or viral infections of the gut, and more generally in the treatment of disease and inflammation. Over the years various techniques for producing immunoglobulins have been proposed. A particularly popular method is for the induction and harvesting of immunoglobulins from ruminant milk. This approach has particular advantages in that the immunoglobulin produced in the milk is in a form suitable for immediate consumption, or may be processed into appropriate formulae or products. It is safe to use and the industry infrastructure for producing milk containing antibodies is already in place.

The ruminant immune system appears to differ from its human counterpart in that the immunoglobulin dominant in bovine mammary secretions is $IgG_1$. Accordingly, the main focus of antibody production in milk by active immunisation has been on immunoglobulin G's, although theoretically, the preferred immunoglobulin would be IgA for the reasons outlined above.

Some attempts have been made to produce increased levels of IgA in ruminant milk. Proposals for vaccination by a single administration route such as parenteral, subcutaneous, intravenous, systemic, oral, intraperitoneal, intramuscular, intramammary and the like have been suggested. Generally, these routes of administration have resulted in the predominant production of $IgG_1$. Systemic immunisation produced both IgA and IgM in milk, but only at low concentrations. The response was enhanced when intramuscular/sub-cutaneous (IM) and intramammary (IMM) immunisation processes were combined (Am. J. Vet. Res[1]). Combinations of intraperitoneal (IP) and intramammary (IMM) infusion have also been shown to produce IgA and IgG, (Immunology[7]; Res. in Vet.Sci[8], Res. in Vet.Sci[11], The Ruminant Immune System in Health and Disease[10]. It is noted that this route leads to limited enhancement of IgA production (The Ruminant Immune System in Health and Disease[10]). A combination of IM and IMM immunisation gave rise to a predominance of $IgG_1$ in the milk (Aus. J. Dairy Technology[6]), as well as increasing generally the levels of $IgG_2$, IgA, and IgM (Am. J. Vet. Res[1]). Significant between animal variability in the antibody titres produced was also noted.

The predominance of the production of $IgG_1$ is consistent with the findings that IgG's produced are the major immunoglobulins in ruminant mammary secretions.

Intramammary immunisation techniques have generally not been preferred as a route for vaccination under field conditions due to the high chance of mammary infection (Aus. J. Dairy Technology[6]). However, other work suggests that this may not be the case (Am. J. Vet. Res[1]).

It should be noted that much of the published literature concerning immunoglobulin production in mammary gland secretions is directed to disease prevention in animals or their offspring. Few are directed to the production of immunoglobulin enriched milk for the purposes of obtaining the immunoglobulins themselves.

An exception to this is a process for the production of a protein concentrate containing immunological factors of lactic origin in Swiss Patent No. 1,573,995. Nearly 20 years ago, this patent disclosed a process for producing milk with a high antibody titre, by intracisternal instillation into the mammary gland, parental injection (subcutaneous, intravenous), injection into the retromammary ganglionic system by scarification, by oral ingestion or by a combination of several of these modes. The only specific immunisation protocol for obtaining colostral and transition milk disclosed involved some 11 immunisation steps over a period of 8 weeks prior to calving. This protocol comprises multiple parental (including intravenous) administration steps, with several IMM administration steps interspersed and requires 2 oral administration steps in the week prior to calving.

This protocol is not in widespread use today. The immunisation plan is onerous in the number of steps involved and is not in fact optimised for immunoglobulin A production. Indeed, the patent is misleading in suggesting that IgA's are preponderant in ruminant maternal milk; a misconception that may have resulted from the knowledge that IgA is predominant in human milk. As established in other teachings (see for example, Aus. J. Dairy Technology[6]), IgG is the predominant immunoglobulin produced in the maternal milk.

It has also been shown in the intervening years that oral delivery of antigens results in little or no increase of IgA titres in mammary secretions when compared with non-inoculated controls (Am. J. Vet. R[1]). It is presumed that the presence of the rumen may preclude the antigen reaching the small intestine. Accordingly, the oral administration step called for by Hilpert is now contraindicated.

Similarly, intravenous injection would not generally be recommended for immunisation purposes because of the possible adverse effects such as anaphylactic shock (Cold Spring Harbour[18], ILAR Journal[19]).

There is currently a need for a process for inducing, and producing IgA in milk at higher levels than have previously been obtained by known antigen administration processes. A process which additionally reduces between animal variability in the production of IgA is also desirable. A commercial process which optimises production of IgA while simplifying the immunisation protocol is also sought.

It is therefore an object of this invention to provide a process for the induction and production of immunoglobulin A in milk which goes some way towards overcoming the above disadvantages or at least provides the public with a useful choice.

Accordingly, the present invention can broadly be said to consist in a process for the induction of immunoglobulin A (IgA) in a mammal which process comprises:
(a) actively immunising a pregnant mammal with an antigen by any two routes of administration selected from intramammary (IMM), intraperitoneal (IP) and intramuscular (IM); and
(b) actively immunising said mammal with an antigen by a third administration route selected from intramammary (IMM), intraperitoneal (IP) and intramuscular (IM); with the proviso that all three administration routes are different.

In a further aspect the present invention provides a process for the production of mammalian milk containing immunoglobulin A (IgA), which process comprises:
(a) induction of IgA according to the process set out above; and
(b) collecting milk containing IgA from said mammal.

Preferably, the initial immunisation protocol is followed by a programme of booster immunisations over the preparturition period.

In a preferred process of the present invention the antigen administered is the same for each route of administration.

Preferably, the antigen administered is emulsified in an adjuvant. A particularly preferred adjuvant is Freunds incomplete adjuvant (FIC).

In one embodiment of the invention IgA may be isolated from the mammalian milk collected. The isolated IgA may be purified if desired.

In a further aspect, the present invention provides mammalian milk containing IgA produced in accordance with the processes of the invention.

In a still further aspect, the present invention provides IgA produced in accordance with the processes of the invention.

Preferred mammals for use in the processes of the present invention are ruminants, especially diary cows.

The present invention further provides for the use of immunoglobulin A produced in accordance with the processes of the invention in pharmaceutical, cosmetic and veterinary compositions as well as in food products including functional foods and dietary supplements.

Although the present invention is broadly as defined above, it will be appreciated by those persons skilled in the art that the invention is not limited thereto and that it also includes embodiments of which the following description gives examples. In particular, preferred aspects of the invention will be described in relation to the accompanying drawings in which: E1

FIG. 1 shows a typical immunoglobulin dilution curve for a positive control sample in the ovine *Escherichia coli* IgA enzyme linked immunoabsorbent assay (ELISA).

FIG. 2 shows the right (immunized) gland milk anti-*Eseherichia coli* IgA titres for all groups on day 0, day4, week 2 and week 4 after parturition.

FIG. 3 contrasts anti-*Escherichia coli* IgA milk responses of the right (immunized) gland and the left (untreated) gland on day 0.

Figure 14:
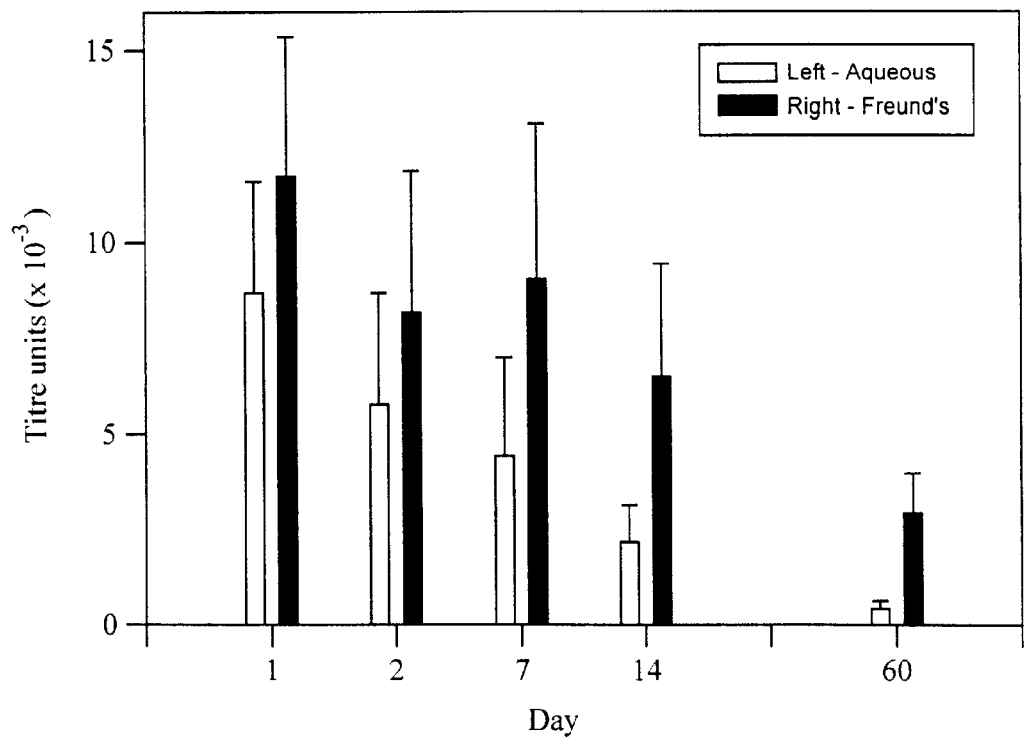

FIG. 14 contrasts the anti-*C. albicans* IgA response in the left gland (aqueous IMM immunogen) and right (FIC IMM immunogen) glands over the lactation period.

DETAILED DESCRIPTION

The term "milk" used herein refers to both milk and colostrum in the form in which it is produced by the mammal.

The term "antigen" as used herein refers to anv material capable of inducing an antigenic response in a treated mammal.

In a first aspect the present invention relates to a process for the induction of immunoglobulin A (IgA) in a mammal. As a first step the method comprises actively immunising a pregnant mammal with an antigen by any two administration routes selected from intramammary (IMM), intraperitoneal (IP) and intramuscular (IM). As a second step the mammal is again actively immunised by a third administration route selected from those routes given above. The proviso to this process is that all three administration routes selected are different.

The applicants have surprisingly found that the use of three routes of administration increases IgA antibody titre levels above what might be expected by simply combining two known administration route processes with a third route of administration, or at least decreases the between animal variability in IgA antibody titre response.

It will be appreciated by the reader that the ordering of the routes and timing of administration is not crucial to the process for inducing immunoglobulin A. Moreover, the immunisations by the different routes may be carried out sequentially, discontinuously or concurrently. A presently preferred immunisation protocol is for concurrent IM and IP immunisation followed by IMM immunisation. The IM and IP immunisations effectively act to prime the immune system response. The IMM immunisation is a localised challenge to induce IgA production in that immunised region.

In a further preferred embodiment the initial immunisation protocol is followed by a number of booster doses of antigen over the pre-parturition period. The amounts of antigen introduced, the frequency (time interval), and the number of booster doses may vary widely. For example, from a single booster shot via a single route of administration on one occasion through to multiple shots via each of three administration routes on many different occasions.

Booster shots are generally spaced to suit the convenience of the operator. To avoid local irritation and congestion, it is usually preferred that booster shots to the same site not be given more frequently than every other week.

One regimen preferred requires concurrent IM and IP immunisation on two separate occasions, followed by IMM immunisation on one occasion. That is, effectively two priming steps followed by local challenge. The first priming step is generally carried out 2 to 8 weeks before the second priming and challenge steps. These latter steps are desirably carried out concurrently. A convenient protocol is for the first priming step to be effected 6 to 14, preferably 8 to 12, and most desirably, 8 weeks before parturition and the second priming/local challenge step to be effected 2 to 10 weeks, preferably 4 to 8, and most desirably, 4 weeks before parturition. However, as noted above timing is not crucial.

A second preferred regimen is for initial immunisation 6 to 14, preferably 8 to 12 and most desirably, 8 weeks before parturition followed by 1 or 2 booster shots via each of the three administration routes on 1 to 3 occasions before parturition. The final immunisation will generally be given 1 to 2 weeks before parturition.

Particularly preferred is a regimen requiring one additional priming and local challenge step such that at 8 weeks prior to parturition (minus 8 weeks) there is a concurrent IM and IP immunisation, followed by concurrent IM/IP and IMM immunisations at minus 4 weeks, a second IMM immunisation at minus two weeks, and a final concurrent IM and IP immunisation at minus one week.

A further preferred regimen is for the initial IM/IP immunisations to be effected at 12 weeks before parturition and the second priming/local challenge step at 8 weeks before parturition, a second IMM immunisation at minus 6 weeks and a final concurrent IM/IP immunisation at minus 4 weeks.

It will be appreciated from the above that a wide variation in the timing of the immunisations is feasible generally starting 14 weeks prior to parturition, but preferably 12 or 8 weeks prior to parturition.

Subsequent to parturition, declining antibody concentrations can be increased by periodically introducing boosters shots of the selected antigen into the mammal during the lactation period according to equivalent pre-parturition protocols outlined above. Generally, this involves between 1 to 6, preferably 2 to 4, and most preferably 2 or 3, concurrent IM and IP immunizations in the lactation phase following parturition together with 1 IMM immunization at the involution stage of lactation.

In a further embodiment of the invention the process of the invention further comprises a preselection step. In this step individual animals are tested and selected for their ability to produce IgA.

As noted above, considerable between animal variability exists for the production of immunoglobulins. This preselection step wherein the animals showing the best IgA antibody titre responses are selected assists in decreasing the between animal variability factor. This process may similarly be used to build groups of animals particularly suited to IgA production.

Processes for IM, IP and IMM administration are well known in the art. For IM immunisation it is generally preferred that more than one site be used for administration by this process. Preferred sites for IM administration are the left and right sides of the brachio cepalic muscle (that is, two sites in one muscle). For IP immunisation, administration into the peritoneal cavity, generally at only one site is presently preferred. Desirably, administration is at the sub lumbar fossa. The precise sites of administration for these routes may of course vary according to known administration protocols. The amount and form of the antigen administered will also vary according to the antigen used and the mammal to be immunised in accordance with known vaccine formulations.

Generally, the antigen is injected using the syringe and needle for IM and IP routes and fine-bore polyethylene surgical tubing fitted to a syringe for the IMM route or alternatively a conventional sterile intra mammary applicator. For the IMM immunisation, the antigen is generally administered via the major lactiferous duct or the supramammary lymph node. Preferably, via the teat orifice into the teat canal. For best results it is also preferred that each mammary gland be immunised on each occasion. This maximises the localised IgA response mounted in the mammal.

The volume of antigen injected will vary according to the mammal and the route of immunisation. Table 1 below is a summary of the injection volumes for sheep and cows immunised via the IM, IP and IMM routes.

TABLE 1

|  | IM | IP | IMM |
|---|---|---|---|
| Sheep |  |  |  |
| volume | 1.0 ml (per site) | 1.0 ml | 1.0 ml (per gland) |
| maximum volume | 5.0 ml | 2.5 ml | 2.0 ml (per gland) |
| Cows |  |  |  |
| volume | 2.0 ml (per site) | 4.0 ml | 2.0 ml (per gland) |
| maximum volume | 8.0 ml | 10.0 ml | 5.0 ml (per gland) |

Typically for immunising the bovine, antigen is administered at 2 ml per site and 2 sites for IM, 4 ml at 1 site for IP and 2 ml into each of the four glands for IMM.

Contrary to conventional wisdom, field trials show that there is no significant risk of infection using intramammary immunisation provided appropriate precautions are taken. For example, care must be taken to sterilise glands prior to immunisation. Appropriate sterilisation methods are known in the art. For example, ethanol/iodine washes will serve this purpose. A further precaution is to ensure that the antigen is administered in a solution containing antibiotic. Suitable antibiotics include dupocillin and ampicillin and clavulox L.C.

The mammals selected for use in the process of the invention will generally be economically useful mammals such as ruminants. Examples of the ruminants preferred for use are cows, goats, and sheep.

The term "antigen" as used herein refers to any material capable of inducing an antigenic response in the treated mammal. Antigens may be selected according to the ultimate utility of the IgA formulation. That is, if the formulation is to be used for generating passive immunity, the antigen against which such immunity is sought should be used. Antigenic substances which may be employed in the process of the invention include bacteria, viruses, yeasts, mycoplasmas, proteins, haptens, animal tissue extracts, plant tissue extracts, spermatozoa, fungi, pollens, dust, chemical antigens and mammalian cells.

Where haptens are to be used as antigens these should first be conjugated to carrier substances such as proteins using chemistry well known to people versed in the art. (ILAR Journal[19]).

Useful bacterial antigens include species of Escherichia, Staphylococcus, Streptococcus, Salmonella and Pneumococcus.

Particularly preferred bacterial antigens are *Escherichia coli, Clostridium difficile,* Vibriocholerae, and *Helicobacter pylori.*

Preferred yeast antigens include species of Candida.

A particularly preferred yeast antigen is *Candida albicans*.

Useful viral antigens include Rotavirus, herpes, fowlpox, rhinopneumonitis, Coronavirus, parvovirus and influenza. Protein antigens include tumor necrosis factor, insulin-like growth factors, and somatostatin, viral or bacterial cell surface proteins and conjugated protein antigens. Chemical antigens include pollens, pesticides, insecticides, fungicides and toxins. Complex antigens comprising a combination of two or more antigens of the types identified are also feasible. One such preferred complex antigen is 3K Scourguard (SmithKline Beecham, Royal Oak, Auckland, New Zealand). The vaccine contains pathogenic *E. coli*, bovine Rotavirus, and Coronavirus.

Useful Mycoplasma antigens include *Mycoplasma pneumoniae* and *Cyptosporidium parvum*.

Generally, the antigenic substances are suspended in liquid medium for infusion or injection according to known protocols. Any appropriate carriers, diluents, buffers, and adjuvants known in the art may be used. Suitable suspension liquids include saline solution, water, and physiologic buffers.

The use of adjuvants is also desirable. Suitable adjuvants for use with the antigens of the invention include Freund's complete adjuvant (FCA), Freund's incomplete adjuvant (FIC), adjuvant 65, cholera toxin B subunit, aluminum hydroxide Al(OH)3; or *Bordetella pertussis,* muramyl dipeptide, cytokines and saponin. Oil based adjuvants and in particular FCA and FIC are preferred.

Prior to injection antigens in appropriate carriers are typically emulsified with oil-based adjuvant (FIC is preferred) using a laboratory homogeniser. Aqueous antigen is typically mixed with 3 volumes of oil adjuvant and emulsified until a stable water in oil emulsion is formed as demonstrated using tests well known in the art.

Conventional wisdom also taught that the use of oil based adjuvants with direct intramammary immunisation was not feasible because of the risk of adverse reactions. The present applicants have found that not only is the administration with oil based adjuvants feasible under appropriate care conditions, but is also desirable. The use of FIC may significantly enhance the immunogenic response obtained for some antigens, particularly when administered by the IMM route. It is therefore presently preferred that antigens be emulsified in FIC for all immunisations except for small polypeptides where FCA may be preferable for the first IM/IP immunisation. However, FCA has not been used for IMM.

As noted above, the size and concentration of the antigen doses are not critical and it is known in the art that there is a dose range known as the window of immunogenicity for antigen and that this is generally relatively broad.

However, too much or too little antigen may induce suppression, tolerance or immune deviation towards cellular immunity and away from humoral immune response. Typically, for protein antigens optimal doses are of the order of 5 to 25 μg/kg live weight in ruminants and for dead, lyophilised bacterial or viral antigens doses in the range of $1 \times 10^8$ to $4 \times 10^{10}$ organisms per ml are typical.

As also noted above, in IMM immunisation it is preferred that the antigen additionally be formatted in suspension with an antibiotic.

Regarding the specific form of the antigen, it will be appreciated by the reader that both live and killed vaccines are possible. Studies have shown that killed vaccines will stimulate $IgG_1$ responses while live vaccines stimulate $IgG_2$ responses. For the production of IgA either alternative is possible.

The antigen administered by each of the immunisation routes may be the same or different. Accordingly, several different antigens may be administered by the three different immunisation routes for each of the initial and booster immunisations. However, it is presently preferred that the same antigen or combination of antigens be administered via the three routes on each immunisation occasion.

In a further aspect the present invention relates to a process for the production of mammalian milk containing IgA which method comprises induction of IgA antibodies according to the process detailed above and then collecting the IgA containing milk from the mammal. The collection of milk may be effected using normal milking processes.

IgA titre responses are generally highest on the first day following parturition. After this antibody levels drop to between 5 to 20% of the initial level. This subsequent level is usually maintained for two to three months or until drying off or involution. IgA levels may be raised in this period through booster immunisations as discussed above. Milk containing IgA may usefully be collected throughout this period.

This milk is useful in the form obtained directly from the mammal but may be processed if required. Examples of processing steps include heat treatment, ultra violet radiation, concentration, supplementation with food additives, drying into concentrates, milk powders and the like.

As a further step to the process of the invention, the IgA may be isolated from the milk. Isolation may be effected using separation techniques known in the art. For example, isolation of immunoglobulin rich fractions from whey in Can. J. Vet. Res[21], EP 0320152, WO 97/27757, GB2179947, from milk in Milchwissenschaft[22], U.S. Pat. No. 4,229,342, from colostrum in Agric. Biol. Chem[20], French Patent No.2520235, New Zealand Patent No. 239466 and U.S. Pat. No. 4,582,580, and from milk and colostrum in U.S. Pat. No. 4,644,056.

The isolated IgA may subsequently be purified if desired. Purification may be carried out according to known techniques such as precipitation and ion exchange chromatography. Suitable techniques are disclosed in the journals and patents referenced above. Both the isolated and purified immunoglobulin A produced in accordance with the additional process steps also form part of the present invention.

In a further aspect the present invention relates to mammalian milk containing IgA produced in accordance with the process of the invention.

Processes for producing protein concentrates containing immunoglobulins on a commercial scale are disclosed in Swiss Patent No. 1,573,995 incorporated herein by reference. Briefly, the process comprises collecting the milk of hyperimmunised milk-bearing females; separating the cream and the impurities, coagulating the clarified and skimmed milk, separating the casein, filtering, ultrafiltering and sterilising the proteins of the whey by filtration, evaporating and drying the product under conditions which do not denature the immunoglobulins and which maintain sterility.

In a further aspect, the present invention provides for the use of IgA in the form of milk, processed milk products, concentrates, isolated IgA and purified IgA produced in accordance with the process of the invention. IgA has potentially broad applications in the fields of pharmaceutical, veterinary and cosmetic compositions as well as in foods and dietary supplements. Such compositions, food and supplements can be administered to patients (including human patients) having need of same.

More specifically, in the human health care field passive oral immunization using milk immunoglobulins from specifically vaccinated cows has long been known. Given the significant role that IgA plays in preventing enteric infections, formulations containing IgA may be effective in treating patients susceptible to such enteric infections. Formulations containing IgA antibodies against enterotoxigenic gastric pathogens including pathogenic *E. coli*, Rotavirus, Staphylococcus, Streptococcus, Aerobacter, Salmonella, Pseudomonas, *Haemophilus influenza, Proteus vulgaris, Shigella dysenteriae, Diplococcus pneumonae*, Coronavirus and Corynebacterium acne are all possible.

Formulations containing high levels of IgA specific for infants is one application. Infants are often very susceptible to enteric gastric disorders. Specific formulations containing anti-cryptosporidiosis IgA for protection against cryptosporidiosis infection in HIV and AIDS patients is a further possibility. General formulations for protection of travelers against diarrhoea and general gastric disorders are contemplated. Valuable formulations containing antibodies against *Helicobacter pylori* for protection against stomach ulcers are feasible.

Appropriate formulations can be produced based on known art formulations. For example, formulations for treating the following disorders are provided for in the art:

| Treatment of | Reference |
|---|---|
| Gastroenteritis | Swiss Patent No. 1,573,995 |
| Infantile *E. coli* gastroenteritis | Eur. J. Pediatr[14] |
| Enteric infections | Advances in Exp. Med. & Biol.[15] |
| Enteric disease | U.S Pat. No. 5,066,491 |
| Campylobacter jejuni | J. Applied Bacteriology[25] |
| Shigella Flexneri | Am. J. Tropical medicine and Hygiene[27] |
| Rotavirus diarrhoea | Indigenous Antimicrobial Agents[23] |
| Dental Caries | Infection and Immunity[28] |
| Cryptosporidial diarrhoea | Lancet[24], Gastroenterology[29] |
| Cryptosporidiosis in AIDS | Archives of Disease in Childhood[30] |
| Rotavirus gastroenteritis | J. Infectious Diseases[16], J. Clinical Microbiology[17] |
| *H. pylori* | U.S. Pat. No. 5,260,057 |
| Respiratory disease | U.S. Pat. No. 5,066,491 |
| Cryptosporidlosis | U.S. Pat. No. 5,066,491 |

A comprehensive review of the use of bovine immunoglobulins to treat or prevent certain human diseases caused by *H. pylori, C. parvum, E. ccli, S. flexneri, C. difficile, V cholerae*, and Rotavirus is provided in the proceedings of the IDF seminar on Indigenous antimicrobial agents of milk.[23]

In a more general context, pharmaceutical formulations containing IgA tailored to the needs of the young, old, medically impaired, and terminally ill are all desirable.

The formulations of the invention similarly have applications in the veterinary field. For example in the preparation of formulations containing specific IgA antibodies against pathogenic microbiologics such as *E. coli*, Rotavirus, Coronavirus and other scour causing microbes for the prevention and treatment of gastric disorders in neonatal livestock.

Formulations containing specific IgA antibodies against mycotoxins, phytotoxins, aflotoxins, herbicides, pesticides and fungicides to block absorption of these following oral ingestion are possible.

More generally, formulations may be prepared containing IgA against undesirable food ingredients to block their absorption.

As well as pharmaceutical and veterinary formulations, IgA antibodies produced in accordance with the present invention have applications in the nutritional fields. This may range from the use of the milk per se to specific formulations produced containing high IgA levels for well-being, for applications such as nutritional beverages and sports nutrition.

Formulations containing specific IgA against common allergens such as pollens, dust, and mites for allergy protection are possible. Contemplated herein are formulations containing specific antibodies against mycotoxins, phytotoxins, aflotoxins, pesticides, herbicides, environmental pollutants such as dioxins, polychlorinated biphenyls and fungicides to block absorption of these compounds. Formulations against undesirable food ingredients such as cholesterol to block absorption of these would be particularly useful. In a further aspect the specific IgA may be complexed to probiotics or growth factors for the preparation of formulations for gastric well-being.

In the veterinary corollary, formulations containing IgA for nutritional support particularly of economically important animal offspring such as lambs, piglets, calves, foals and chickens are possible. Formulations consisting of specific IgA directed against undesirable food ingredients such as β carotene to block absorption of these may also be useful.

A further area of application for the IgA product of the present invention is in formulations containing the antibodies against skin or hair protein antigens for topical applications, against skin antigens complexed to UV absorbing compounds such as zinc for long-lasting protection against sunburn and with specific IgA antibodies complexed to growth factors for skin repair.

The formulations may be prepared in the form of drinks, lotions, powders, creams and the like according to principles well known in the art. The formulations may be for oral, intravenous, intramuscular, subcutaneous, rectal, topical, parenteral administration or such other routes as may be desired.

The formulations may include pharmaceutically acceptable carriers or, in the case of nutritional supplements, nutritionally acceptable carriers. Such carriers include aqueous solutions, non-toxic excipients, including salts, preservatives, and buffers. The formulations may include additives such as minerals, vitamins, flavouring agents, scenting agents and the like.

General assistance in the preparation of such formulations may be obtained from Remingtons Pharmaceutical Sciences, 16th Edition. Easton: Mac Publishing Company (1980); the National Formulary XIV, 14th Edition. Washington: American Phannaceutical Association (1975); and Goodman and Gillmans The Phannacological basis for Therapeutics (7th Edition) the contents of which are hereby incorporated by reference.

Specific non-limiting examples of the invention will now be described.

EXAMPLE 1

64 pregnant ewes were selected and divided into eight groups and immunised by intra muscular (IM), intra peritoneal (IP) or intra mammary (IMM) routes or combinations of these three. For the IMM immunisation the right gland only was immunised while the left gland was untreated and acted as the control.

Immunisation Protocol

| Group (n = 8) | Immunisation Route |
|---|---|
| 1 | IM |
| 2 | IP |
| 3 | IMM |
| 4 | IM/IP |
| 5 | IM/IMM |
| 6 | IP/IMM |
| 7 | IM/IP/IMM |
| 8 | NIL (Control) |

Animals were immunised according to the following schedule.

Immunization Schedule

| I −8 wk | II −4 wk | III −2 wk | IV −1 wk | 0 | V +4 wk | VI +8 wk | VII +12 wk |
|---|---|---|---|---|---|---|---|
| | | | | Parturition n | | | Weaning |
| IM-1 | IM-2 | | IM-3 | | IM-4 | IM-5 | IM-6 |
| IP-1 | IP-2 | | IP-3 | | IP-4 | IP-5 | IP-6 |
| | IMM-1 | IMM-2 | | | | | IMM-3 |

Antigen

A commercially available pathogenic *E. coli* vaccine (Suvaxyn, Matemafend-4; J&H Pacific Ltd. NZ) was used as antigen. This vaccine is know to have high concentrations of K88, K99, 987P and F41 pili antigens.

Details of the immunisation protocols are as follows:

Immunisation I.

IM/IP

Stock vaccine was emulsified with Freund's Incomplete Adjuvant (FIC; 1 part vaccine: 3 parts FIC).

IM; 1 ml per site; 2 sites
IP; 1 ml per site; 1 site

Immunisation II.

IM/IP

Repeat IM/IP as for Immunisation I.

IMM

Stock vaccine was diluted in sterile saline (1 part vaccine: 1 part saline). Antibiotic (Dupocillin) was added to the IMM immunogen in the ratio of 1 ml antibiotic: 30 ml immunogen.

IMM; 1 ml per gland; right gland only

Immunisation III

IMM

Repeat Immunisation II for IMM only.

Immunisation IV, V and VI

IM/IP

Repeat Immunisation I

Immunisation VII

IM/IP & IMM

Repeat Immunisation II

Animal Health Status

The general health of the ewes in the trial was monitored by regular weight checks and veterinary inspections. There was no discernible difference observed in weight gain/loss between the treatment groups. No adverse effects of immunisation were observed. Two of the 64 ewes were treated for mastitis, one ewe from Group 6 (IP/IMM) and one ewe from Group 7 (IM/IP/IMM). Overall, no deleterious effects of IMM immunisation were noted.

Samples

The ewes were bled before Immunisation I, II, and IV, prior to lambing. Post parturition samples of blood and colostrum/milk (left and right mammary glands separately) were collected at Day 0 (parturition), 1, 2, 3, and 5, then Week 1, 2 and 3, then Month 1, 2 and 3.

Bloods were collected on ice into EDTA vacutainers. Separated plasma was stored at −20° C. for antibody analysis. Left (untreated) and right (immunised) mammary gland colostrum/milk samples (20–30 ml) were kept on ice until centrifuged (4° C.; 20 minutes; 2,000 $g_{max}$) to remove fat. Skimmed supernatant was re-centrifuged (4° C.; 1 hour; 40,000 $g_{max}$) to separate milk whey/plasma and casein. Supernatant was stored at −20° C. for antibody analysis.

Sample Analysis

All samples and reagents were diluted with 0.01M phosphate buffered saline (pH 7.5) containing 0.05% v/v Tween-20 (PBS-T) and 1% w/v Bovine Serum Albumin (BSA; type A7030, Sigma Chem. Co., USA) and all washes were carried out by an automated plate washer (ELP-35, BioTek Instruments, USA) using PBS-T, unless otherwise stated.

ELISA plates (Maxisorp F-96 immunoplates, Nunc, Denmark) were coated with 100 µl of *E. coli* antigen (Suvaxyn Matemafend-4; J & H Pacific Ltd, NZ) diluted 1:1K in 0.05M carbonate buffer (pH 9.6), incubated overnight at 4° C. and washed three times. Remaining activated sites on immunoplates were blocked by incubating 2 hours at 22° C. with 250 µl PBS-T containing 1% w/v BSA. After washing plates 2 times, 100 µl of 10-fold serial dilutions of test samples (primary antibody; 1:100, 1:1K, 1:10K, 1:100K) were added to duplicate wells. Plates were incubated 2 hours at 22° C. then washed 3 times. 100 µl of second antibody consisting of heavy-chain specific rabbit anti-sheep IgA (1:200K; Bethyl Laboratories, USA) were added to the plates. Plates were incubated overnight at 4° C., then washed 3 times prior to the addition of 100 µl of the enzyme conjugate, goat anti-rabbit Ig conjugated to horse radish peroxidase (1:8K; Dako, Denmark). After a 2 hour incubation at 22° C., the plates were washed 2 times with PBS-T then 2 times with PBS containing no Tween-20 and filled with 100 µl of freshly prepared substrate solution. The substrate solution consisted of 0.1 g/l 3,3',5,5'-tetramethylbenzidine (Boehringer Mannheim, Germany) in 0.1M sodium acetate buffer (pH 5.5) containing 1.3 mmol/l hydrogen peroxide. Following a 30 minute incubation at 22° C., 50 µl of stopping solution, 2M $H_2SO_4$, were added and the optical density (OD) was measured at 450 nm by an automated plate reader (EL311s, BioTek Instruments, USA).

With each ELISA microplate a positive quality control sample (assayed at 1:100, 1:1K, 1:10K, 1:100K and 1:1000K) and a negative quality control sample (assayed at 1:1K) was run with the samples. Absorbance values from these control samples were used in calculations to determine sample antibody titres. The median absorbance between the maximum absorbance of the positive control and the absorbance of the negative control gives a 50% figure. The reciprocal dilution of sample antibody equivalent to this 50% absorbance figure is classified as the antibody titre for the sample.

Figure 1:
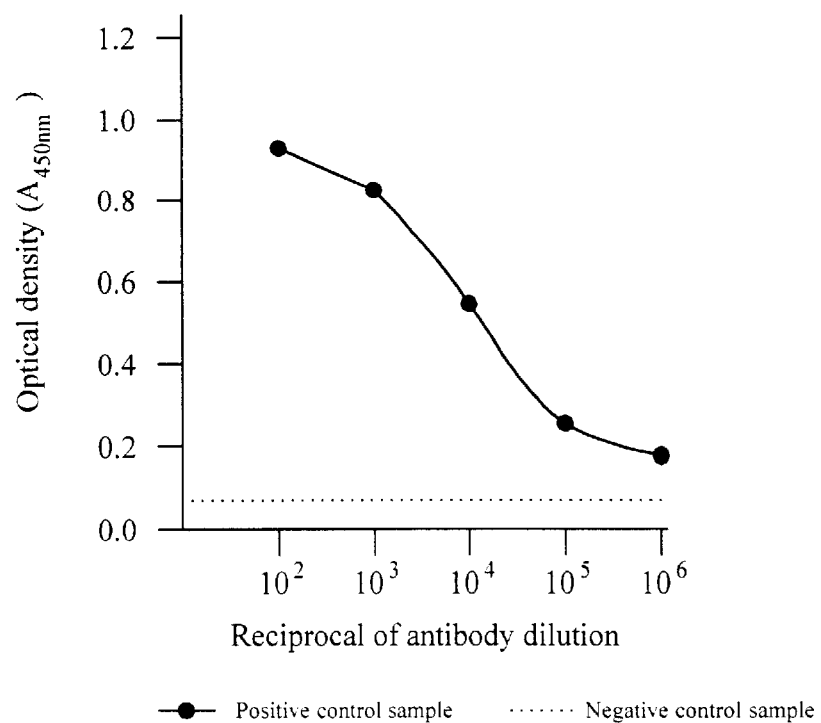

FIG. 1 shows a typical dilution curve for the positive control sample in the E. coli IgA ELISA.

Results

Samples were initially assayed as group pools to obtain an overview of the group responses to the different immunisation regimens.

Figure 2:
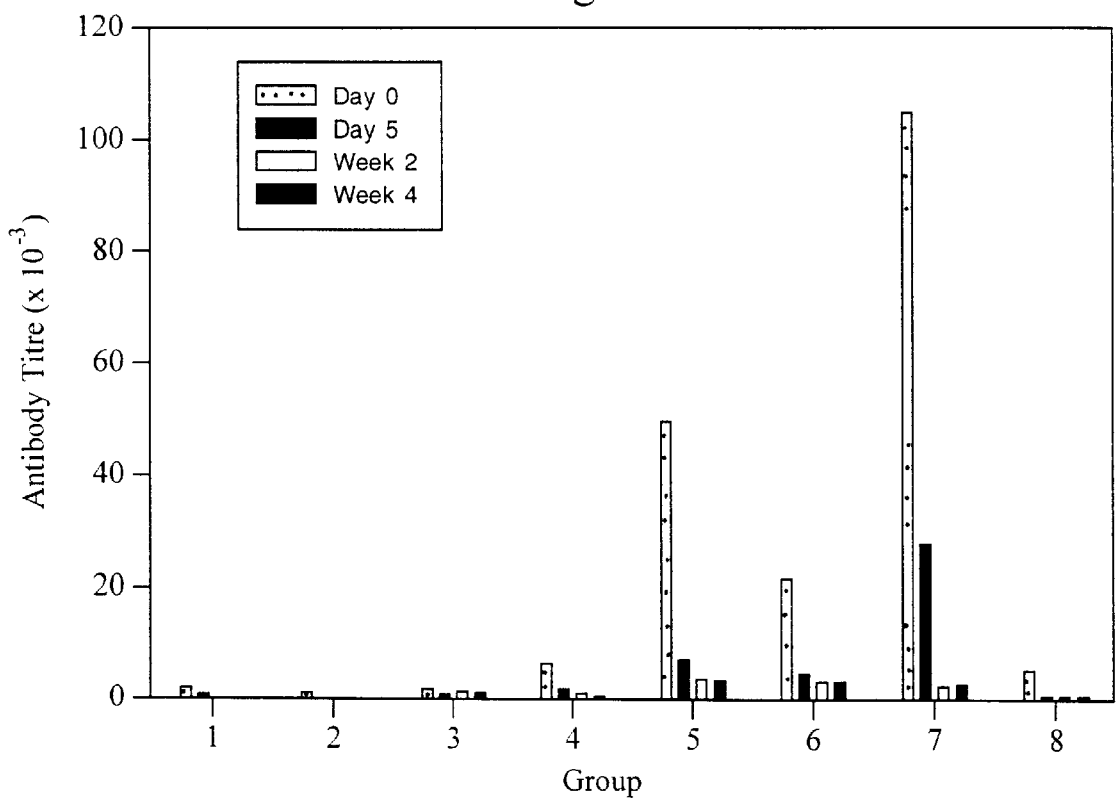

FIG. 2 shows the right (immunised) gland milk anti-E. coli IgA titres for all groups on Day 0, Day 5, Week 2 and Week 4. In all groups, IgA milk antibody titres were highest on Day 0 (parturition) with levels falling over the first week. Group 7 (IM/IP/IMM) gave the best IgA response with a milk antibody titre of 105K. This was followed by Group 5 (IM/IMM) with a titre of 50K and Group 6 (IP/IMM) with a titre of 22K. The other groups gave a minimal response including Group 3 (IMM). By Day 5, the IgA milk antibody titres in Groups 5, 6 and 7 had fallen to about 20% of Day 0 titres but by Week 4 the titres were still significant being approximately 3K.

Figure 3:
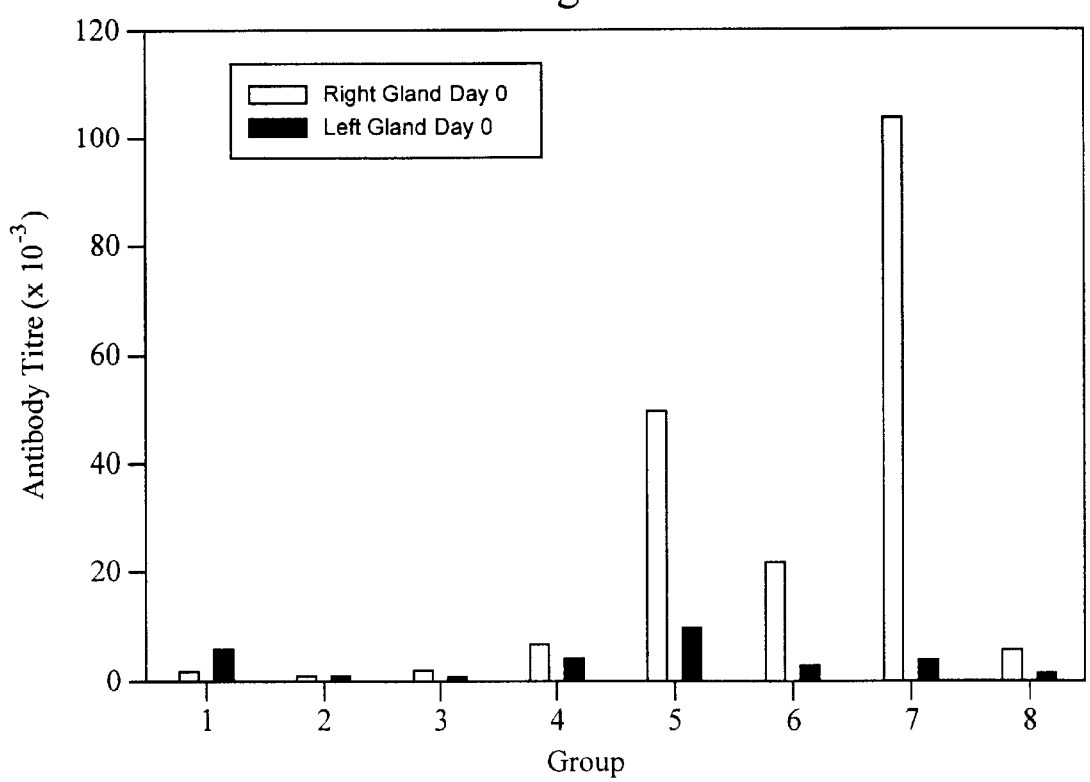

FIG. 3 contrasts anti-E. coli IgA responses of the right (immunised) gland and the left (untreated) gland on Day 0. IgA milk antibody titres showed a marked difference in response between samples from the right (immunised) gland and the left (untreated) gland. While high titres were measured in the right milk samples of Groups 5, 6 and 7, the titres in the corresponding left milk samples were, at best, only 20% of these levels.

above those obtained with the IM/IMM and IP/IMM combinations but serves to decrease the between animal variability in IgA response.

EXAMPLE 3

64 pregnant ewes were selected and divided into eight groups and immunised by intra muscular (IM), intra peritoneal (IP) or intra mammary (IMM) routes or combinations of these three. For the IMM immunisation the right gland only was immunised while the left gland was untreated and acted as the control.

Immunisation Protocol

| Group (n = 8) | Immunisation Route |
|---|---|
| 1 | IM |
| 2 | IP |
| 3 | IMM |
| 4 | IM/IP |
| 5 | IM/IMM |
| 6 | IP/IMM |
| 7 | IM/IP/IMM |
| 8 | NIL - Control |

Animals were immunised according to the following schedule.

Immunization Schedule

| I<br>−8 wk | II<br>−4 wk | III<br>−2 wk | IV<br>−1 wk | 0 | V<br>+4 wk | VI<br>+8 wk | VII<br>+12 wk |
|---|---|---|---|---|---|---|---|
| | | | | Parturition | | | |
| | | | | n | | | |
| IM-1 | IM-2 | | IM-3 | | IM-4 | IM-5 | IM-6 |
| IP-1 | IP-2 | | IP-3 | | IM-4 | IM-5 | IM-6 |
| | IMM-1 | IMM-2 | | | | | IMM-3 |

EXAMPLE 2

Figure 4:
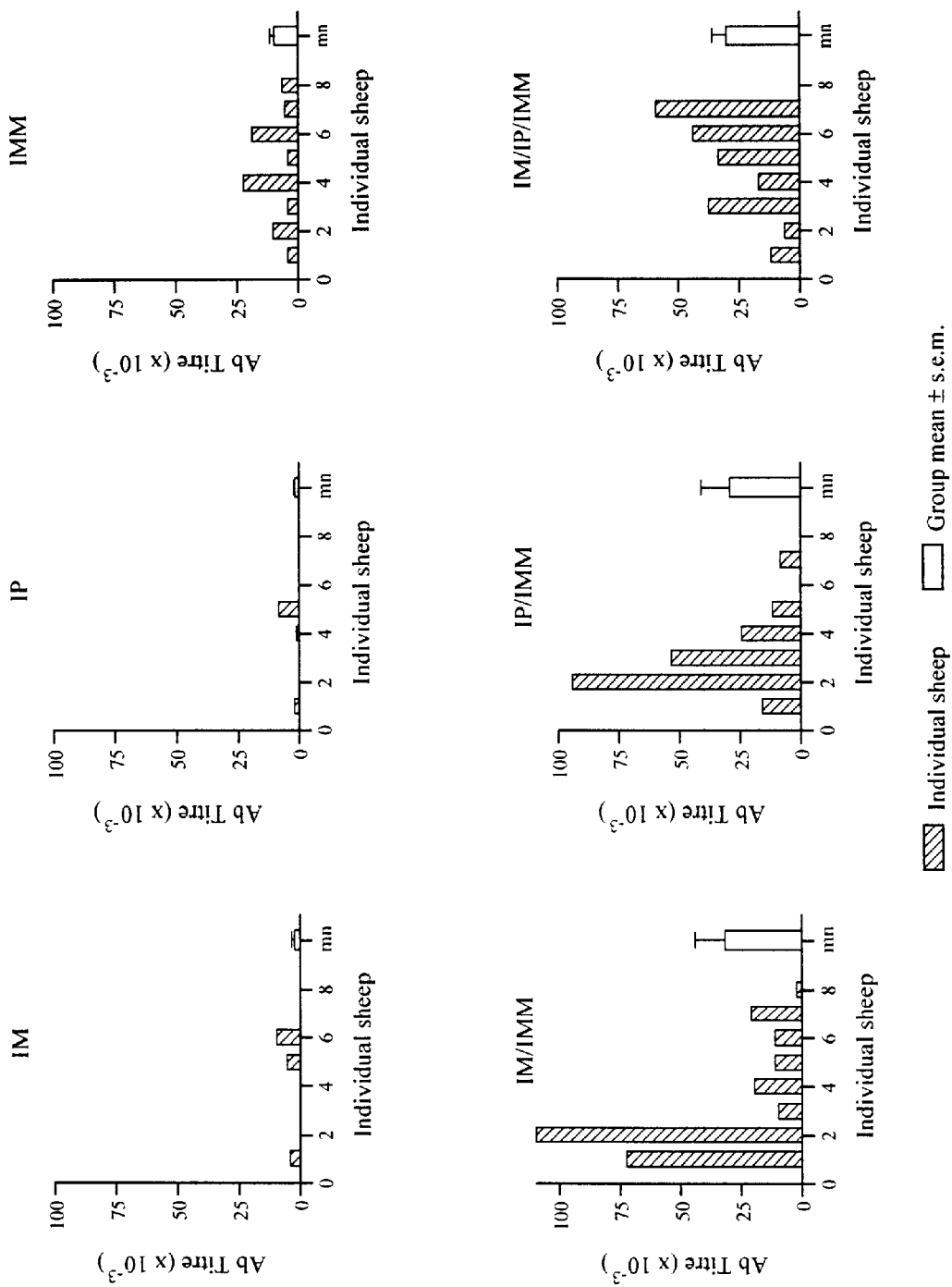
FIG. 4 shows the anti-*Escherichia coli* IgA responses for individual sheep with right (immunized) glands on day 1 post-partum. The effect of the immunization route is depicted.
Figure 5:
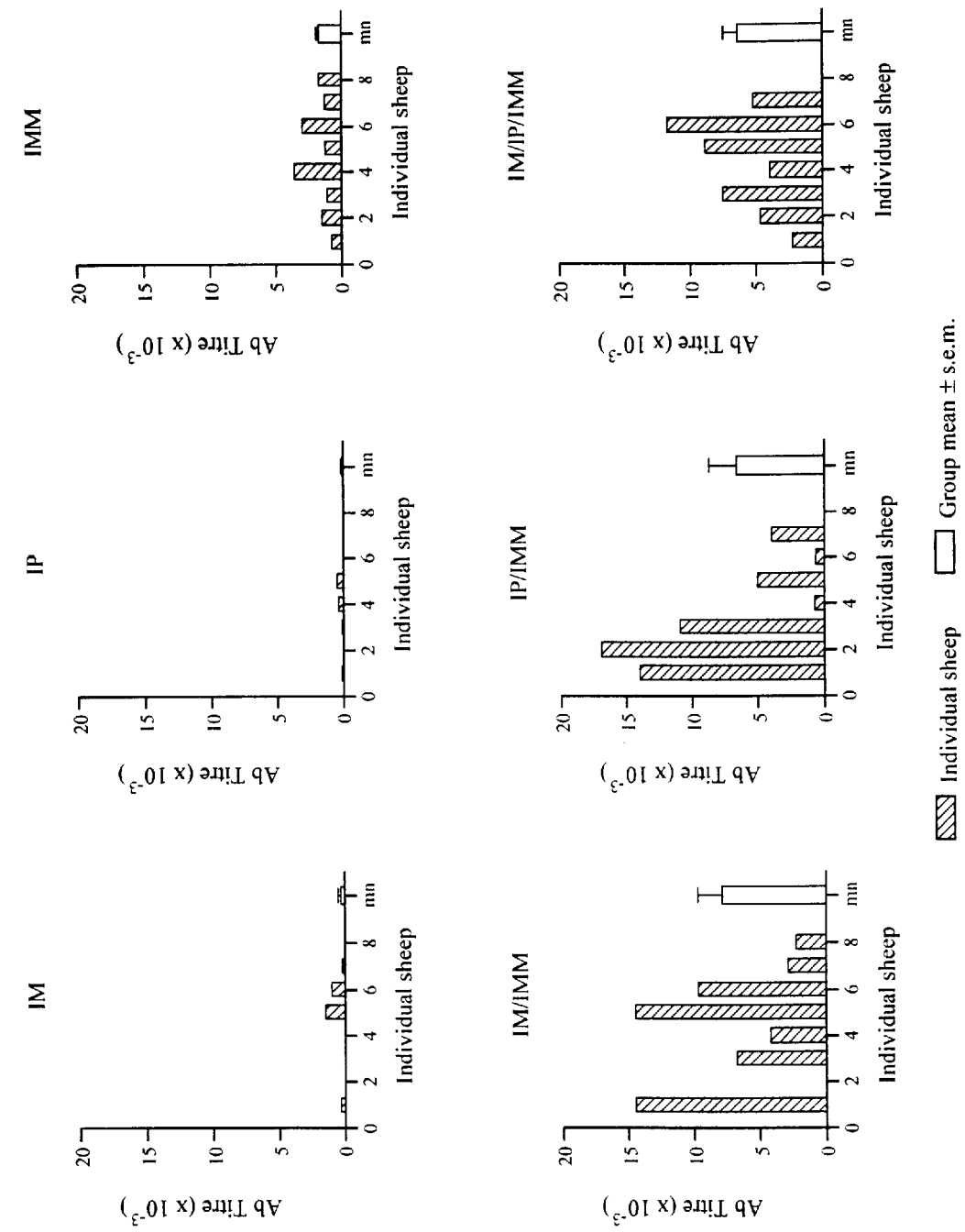
FIG. 5 shows the anti-*Escherichia coli* responses for individual sheep with right (immunized) glands on day 2 post-partum.

Individual samples analysis of anti-E. coli IgA titre responses was conducted for each of the immunisation groups of Example 1. Samples were analysed using the ELISA assay according to the process of Example 1. The results for Day 0 and 1 are shown in FIGS. 4 and 5, respectively.

Results

In general agreement with the earlier pooled data, titres were low in animals immunised by IM, IP or IMM routes alone and much higher in animals treated by the combination IM/IMM, IP/IMM and IM/IP/IMM routes (Mean ±s.e.m. antibody titres; $1/32,100 \pm 1/13,500$; $1/29,000 \pm 1/12,000$; $1/30,000 \pm 1/7,300$, respectively).

No significant differences were observed in mean IgA titre responses resulting from immunisation by each of the three combination routes. However, substantial within-group variability in titre response was observed and notably the standard error of the mean for the IM/IP/IMM group ($1/7,300$) was much lower than that calculated for the IM/IMM ($1/13,500$) and IP/IMM ($1/12,500$) routes.

This pattern of titre response was maintained in milk samples from Day 2 and subsequently. The data appear to indicate that immunisation by the three site IM/IP/IMM procedure does not increase the magnitude of the response Antigen A commercially available vaccine, 3K Scourguard (SmithKline Beecham, Royal Oak, Auckland, New Zealand) was used as immunogen. The vaccine contains pathogenic E. coli, bovine Rotavirus and Coronavirus.

Details of the immunisation protocols are as follows:

The immunisation protocol of Example 1 was repeated with 3K Scourguard used as stock vaccine in place of Maternafend.

Animal Health Status

The general health of the ewes in the trial was monitored by regular weight checks and veterinary inspections. And as for Example 1, there was no discernible difference observed in weight gain/loss between the treatment groups and no adverse effects of immunisation were observed.

Samples

Samples of blood and colostrum/milk were taken according to the protocol of Example 1.

Sample Analysis

The ELISA assay was performed according to the method of Example 1, with the exception that 3K Scourguard (1:1K) was used for microplate coating in place of Maternafend. Blood plasma and colostrum/milk were pooled to obtain an initial indication of group antibody responses.

Results

Figure 6:
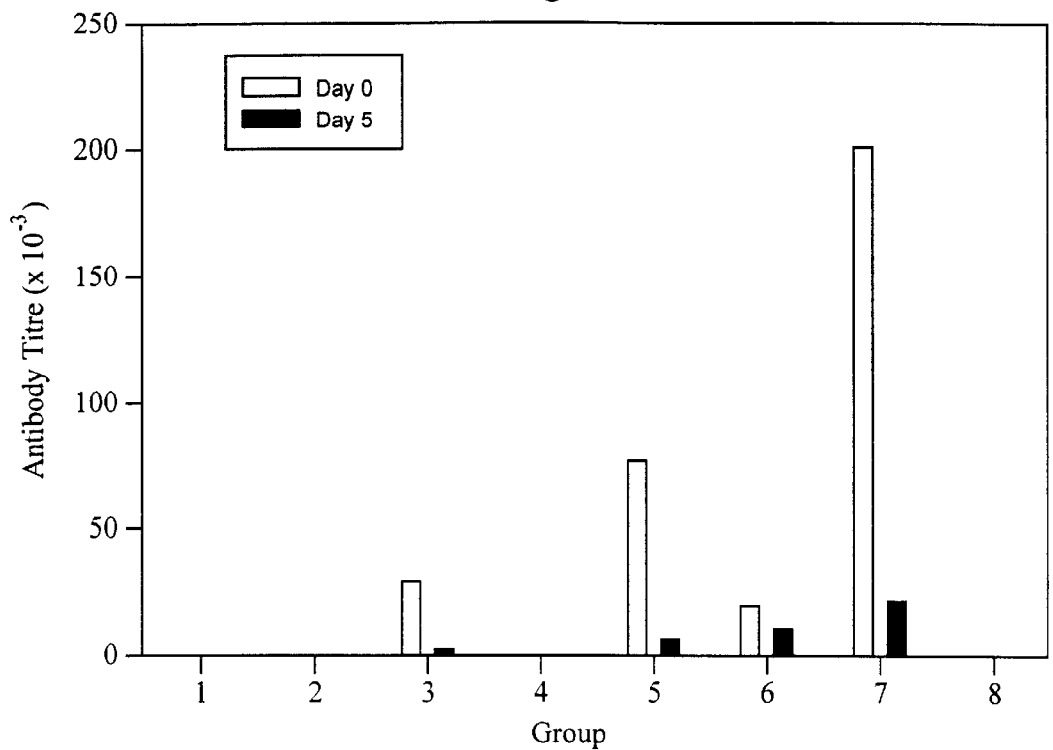
FIG. 6 shows the anti-3K scour guard right (immunised) gland milk IgA antibody titres for all groups on days 0 and 5.

FIG. 6 shows the right (immunised) gland milk anti-3K Scourguard IgA titres for all groups on Day 0 and 5. In all groups, IgA milk antibody titres were highest on Day 0 (parturition) with levels falling over the first week. Group 7 (IM/IP/IMM) gave the best IgA response with a milk antibody titre of 210K. This was followed by Group 5 (IM/IMM) with a titre of 70K and Group 3 with a titre of 27K. Group 6 (IP/IMM) gave a milk antibody response of 20K. The other groups gave a minimal response. By Day 5, the IgA milk antibody titres in Group 3, 5 and 7 had fallen to about 10% of Day 0 titres.

Figure 7:
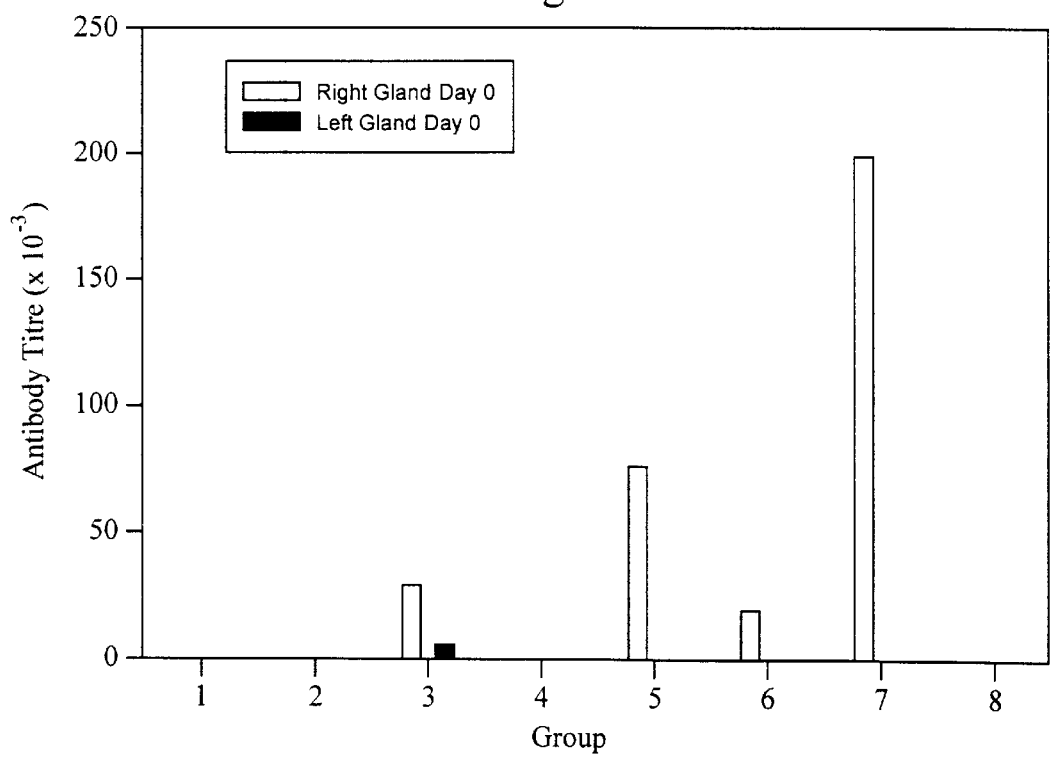
FIG. 7 shows the anti-3K scour guard right (immunised) gland and left gland milk IgA antibody titres for all groups on day 0.

FIG. 7 shows the right (immunised) and left (untreated) gland milk anti-3K Scourguard IgA titres for all groups on Day 0. The right gland had a much greater response than that of the left gland. There was no significant antibody titre response for the untreated left gland except for Group 3.

EXAMPLE 4

32 pregnant ewes were assigned to four treatment groups and immunised by combinations of intra muscular (IM), intra peritoneal (IP) or intra mammary (IMM) routes. IMM immunogen for Group 3 was in aqueous solution while IMM immunogen for Group 4 was emulsified in FIC. For the IMM immunisations the right gland only was immunised while the left gland was untreated and acted as the control.

Immunisation Protocol

| Group (n = 8) | Immunisation Route |
|---|---|
| 1 | IM/IMM |
| 2 | IP/IMM |
| 3 | IM/IP/IMM |
| 4 | IM/IP/IMM(FIC) |

Animals were immunised according to the following schedule.

Immunisation Schedule

| I −8 wk | II −4 wk | III −2 wk | IV −1 wk | 0 |
|---|---|---|---|---|
| ↓ | ↓ | ↓ | ↓ | Parturition |
|  | IMM-1 IMM(FIC)-1 | IMM-2 IMM(FIC)-2 |  |  |
| IM-1 IP-1 | IM-2 IP-2 |  | IM-3 IP-3 |  |

Antigen

A TNF preparation, commercially available from R & D Systems, 614 McKinley Place, New England, USA, was used as antigen. A stock solution (1 mg/ml) was prepared by reconstituting the freeze dried TNF in sterile saline.

Details of the immunisation protocols are as follows:
Immunisation I.
IM/IP
Stock antigen solution was diluted to 0.16 mg/ml then emulsified with FIC (1 part saline: 3 parts FIC).
IM; 1 ml per site; 2 sites
IP; 1 ml per site; 1 site
Immunisation II.
IM/IP
Repeat IM/IP as for Immunisation I.
IMM
For right glands: Stock antigen solution was diluted to 0.1 mg/ml in sterile saline. Antibiotic (Dupocillin) was added in the ratio of 1 ml antibiotic: 40 ml immunogen. IMM; 1 ml per right gland
IMM(FIC)
For right glands: Stock antigen solution was diluted to 0.32 mg/ml in sterile saline and emulsified with FIC (1 part saline: 3 parts FIC). Antibiotic (Dupocillin) was added in the ratio of 1 ml antibiotic: 40 ml immunogen. IMM(FIC); 1 ml per right gland
Immunisation III
IMM/IMM(FIC)
Repeat Immunisation II for IMM/IMM(FIC) only.
Immunisation IV
IM/IP
Repeat Immunisation I Animal Health Status The general health of the ewes in the trial was monitored by regular weight checks and veterinary inspections. The animals maintained weight during pregnancy and lactation and no between group effects of treatment were observed. Two animals died from unrelated causes during pregnancy/lambing (both ewes from Group 1, IM/IMM). One animal was withdrawn from the trial due to mastitis in the left untreated gland. No adverse effects on immunisation were noted. Evidence of ulceration at IM and IP immunisation sites was minimal. No significant differences were observed in mammary function between the left and right glands and between glands immunised with immunogen in sterile saline or FIC.

Samples

The ewes were bled before Immunisation I, II, and IV, prior to lambing. Post lambing, samples of blood and colostrum/milk (left and right mammary glands separately) were collected at Day 1 (parturition), 2, 3, 6, 14 and 28, and Month 2 and 3.

Samples were collected and treated according the format used in Example 1.

Sample Analysis

Figure 8:
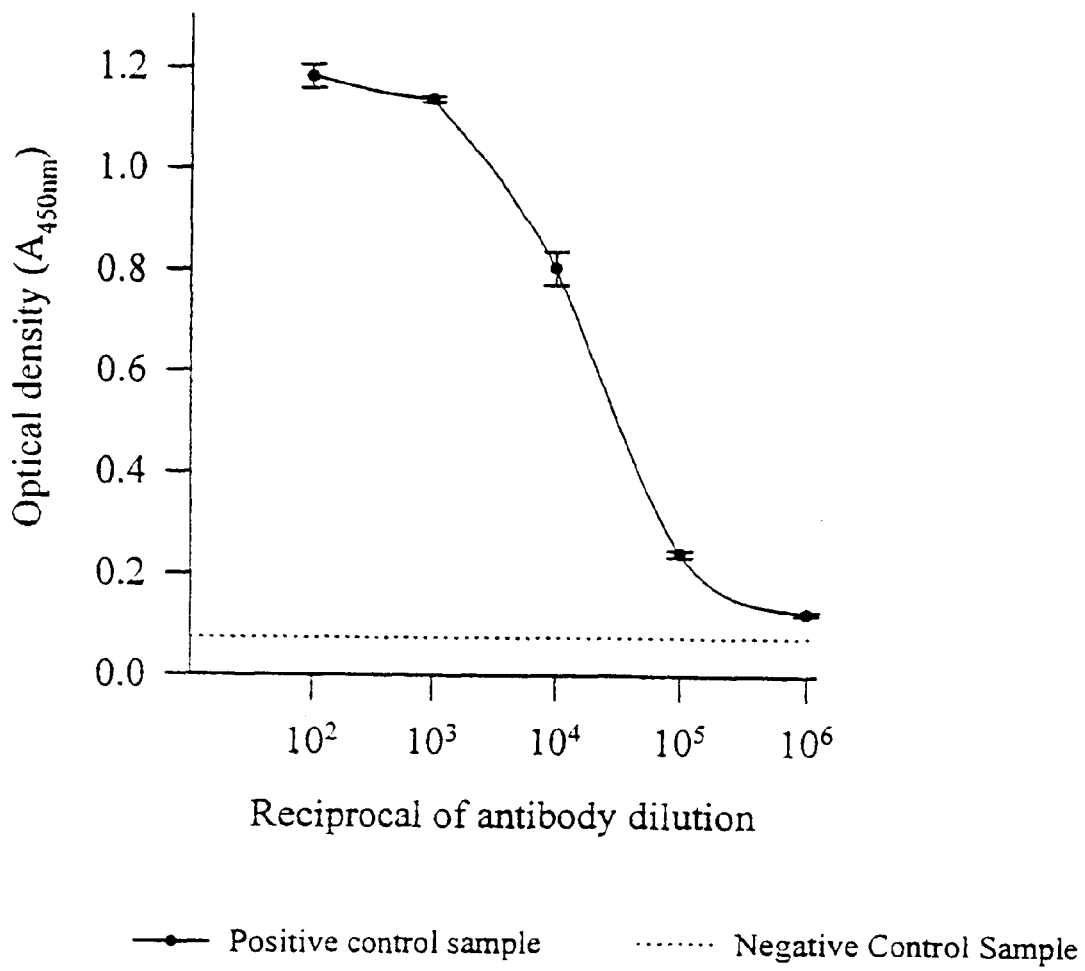
FIG. 8 shows a typical dilution curve for positive and negative control samples in the ovine TNF IgA ELISA.

The ELISA assay for TNF was performed according to the format used for Example 1, with the exception that TNF was used for plate coating (2 mg/ml). FIG. 8 shows a typical dilution curve for the positive and negative control samples in the TNF IgA ELISA. Inter assay precision was calculated from 10 repeat analysis of the positive control and the coefficient of variation was 10.2%.

Results

IgA Milk Responses

Figure 9:
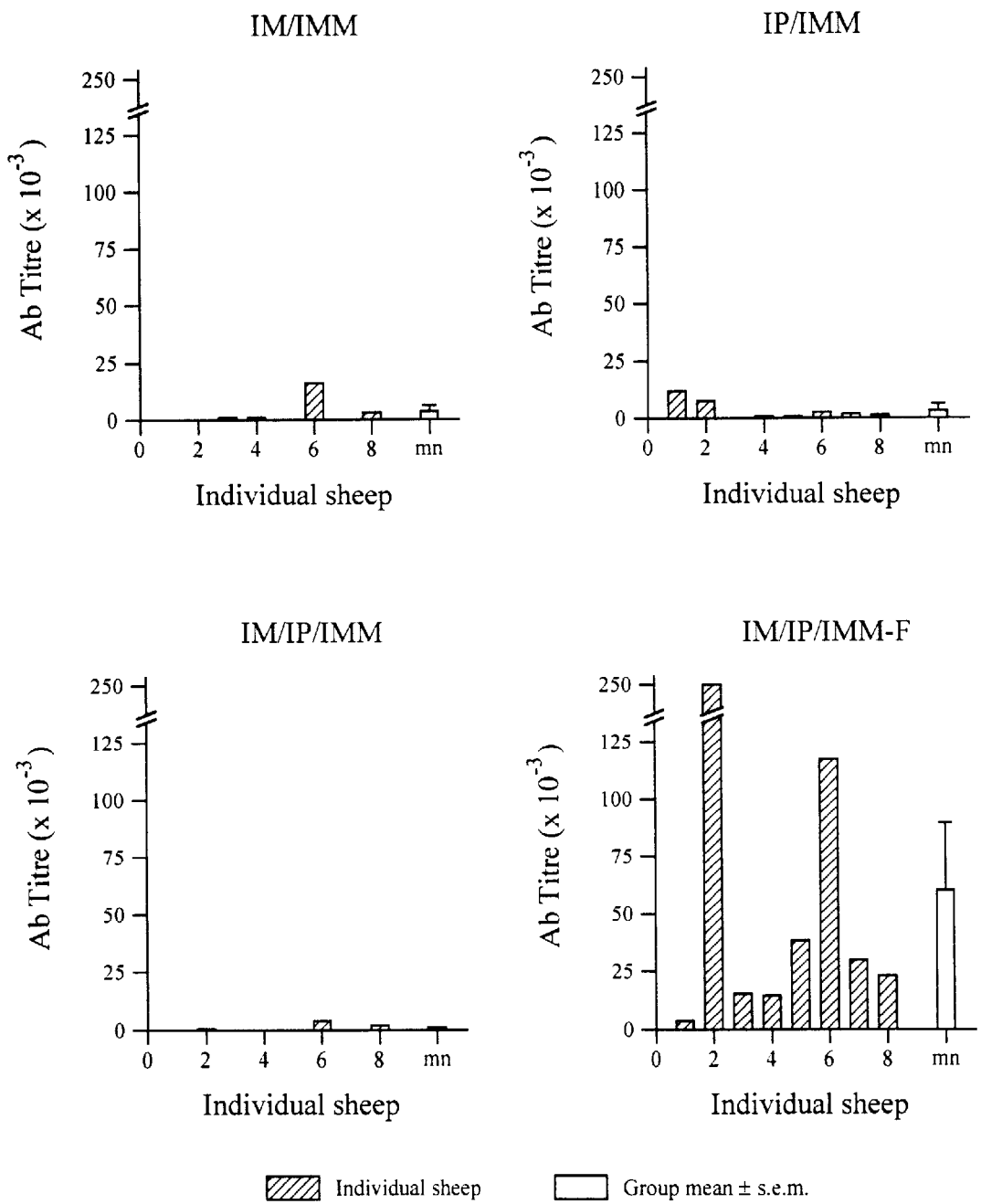
FIG. 9 shows individual sample analyses of anti-TNF IgA titre responses in the right (immunised) gland day 1 postpartum milk samples for each of the immunisation groups.

Individual sample analyses of anti-TNF IgA titre responses in the right (immunised) gland Day 1 postpartum milk samples for each of the immunisation groups are shown in FIG. 9. Titres were low in animals immunised by the IM/IMM, IP/IMM or IM/IP/IMM routes where the immunogen was administered in saline solution. (Mean ±s.e.m. antibody titres: $1/3{,}600 \pm 1/2{,}600$; $1/3{,}300 \pm 1/1{,}500$; $1/900 \pm 1/500$, respectively.) By contrast, titres were some 20-fold higher in animals treated by the combination IM/IP/IMM routes where the IMM immunogen was emulsified in FIC ($1/61{,}900 \pm 1/29{,}600$). Considerable variation was observed in the responses of the individual Group 4 animals with titres ranging from $1/4{,}000$ to $1/250{,}000$.

Right and Left Gland Milk Antibody Responses

Figure 10:
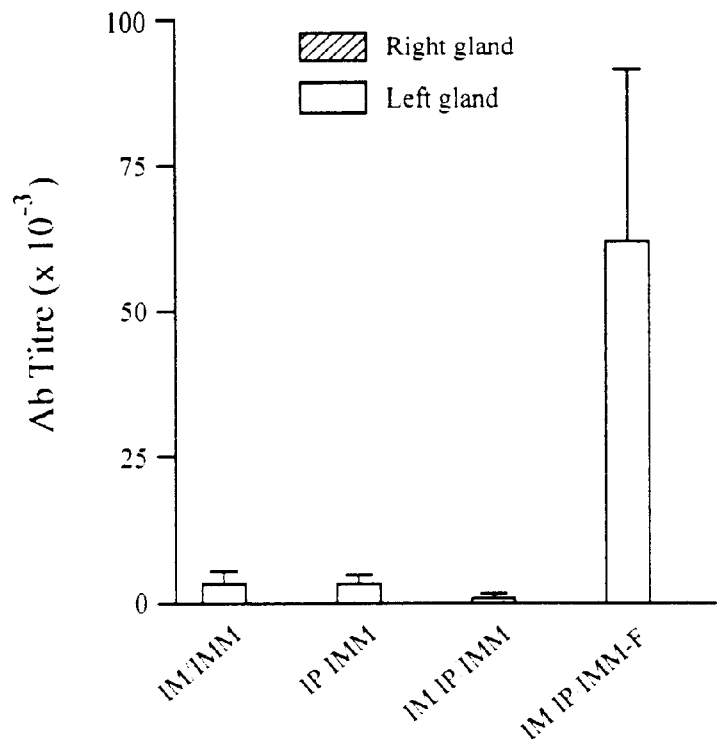
FIG. 10 shows the data for anti-TNF titres from day 1 postpartum samples from the right (immunised) and left (untreated) gland.

Significant differences were seen in anti-TNF IgA milk titres from right (immunised) and left (untreated) glands with the left gland IgA titre being almost undetectable, in agreement with earlier findings for *E. coli*. FIG. 10 depicts the data for anti-TNF IgA titres for Day 1 postpartum milk samples from the left and right glands.

Milk Antibody Response Over Lactation

Figure 11:
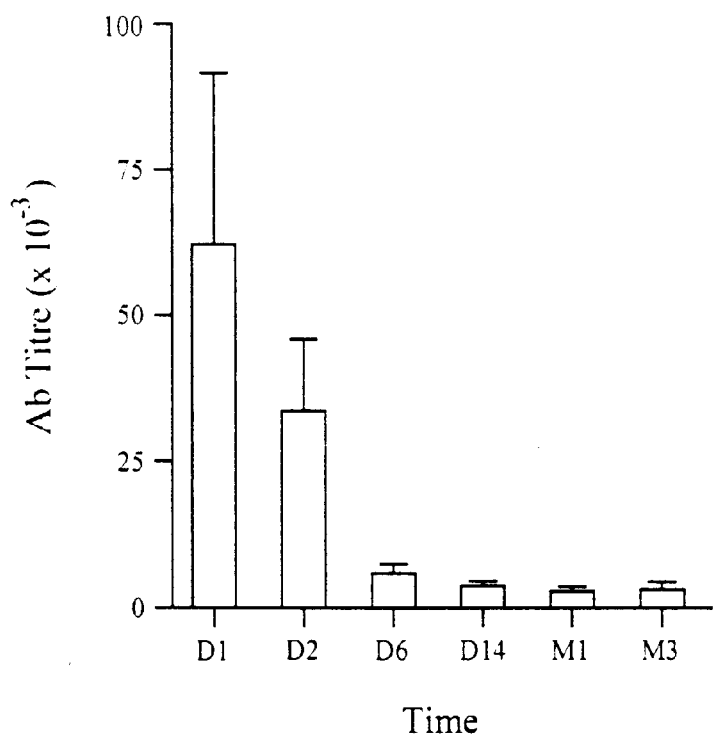
FIG. 11 shows the relationship of anti-TNF IgA to stage of lactation.

The relationship of anti-TNF IgA to stage of lactation is shown in FIG. 11. Data are mean ±s.e.m. right (immunised) gland milk titres from Group 4 animals treated by the combination IM/IP/IMM(FIC) route. Anti-TNF IgA titres were highest in initial post-partum mammary secretions and found to decline to approximately 10% of peak levels by Day 6 and approximately 5% by Month 1 (equivalent to an IgA titre of 1/3,500). The overall pattern of response was similar to that seen in the *E. coli* trial, the antibody decline coinciding with the onset of full lactation and increasing milk volumes.

EXAMPLE 5

35 pregnant cows were divided into four groups and immunised by either two routes, three routes or none according to the protocol below. Immunogen was emulsified in Freund's Incomplete Adjuvant (FIC) for right sided glands intra mammary (IMM) immunisations and for intra muscular (IM) and intra peritoneal (IP) immunisations. Left sided glands utilised immunogen in aqueous solution.

Immunisation Protocol

| Group | Immunisation Route |
| --- | --- |
| 1a (n = 10) | IM/IMM |
| 1b (n = 10) | IP/IMM |
| 1c (n = 10) | IM/IP/IMM |
| 1d (n = 5) | NIL |

Animals were immunised according to the following schedule.

Immunisation Schedule

| I<br>−8 wk | II<br>−4 wk | III<br>−2 wk | IV<br>−1 wk | 0 |
| --- | --- | --- | --- | --- |
| ↓ | ↓ | ↓ | ↓ | |
| | | | | Parturition |
| | IMM-1 | IMM-2 | | |
| IM-1 | IM-2 | | IM-3 | |
| IP-1 | IP-2 | | IP-3 | |

Antigen

Antigen for immunisation was the yeast, *Candida albicans*. The yeast cells were cultured in medium, harvested by centrifugation, washed and heat killed then freeze dried. A stock solution of *C. albicans* (7 mg protein per ml) was prepared by reconstituting the freeze dried *C. albicans* in phosphate buffer.

Details of the immunisation protocols are as follows:

Immunisation I.

IM/IP

Stock antigen solution was diluted to 1 mg/ml in sterile saline and emulsified with FIC (1 part saline: 3 parts FIC). IM; 2 ml per site; 2 sites
IP; 4 ml per site; 1 site Immunisation II.

IM/IP

Repeat IM/IP as for Immunisation I.

IMM

For right glands: Stock antigen solution was diluted to 1 mg/ml in sterile saline and emulsified with FIC (1 part saline: 3 parts FIC).

For left glands: Stock antigen solution was diluted to 0.25 mg/ml in sterile saline. IMM; 2 ml per gland; 4 glands Immunisation III

IMM

Repeat Immunisation II for IMM only.

Immunisation IV

IM/IP

Repeat Immunisation I

Animal Health Status

The general health of the cows in the trial was monitored by regular weight checks and veterinary inspections. Immunisation sites were inspected at regular intervals to assess effects of the immunisation procedure. No clinical grade site reactions were observed at any of the sites immunised. In addition, milk volume data collected indicated that treatment of the mammary gland did not effect the overall lactation performance of the animals.

Samples

The cows were bled before Immunisation I, II, and IV, prior to calving. Post parturition samples of blood and colostrum/milk were collected at Day 1, 2, 3, 5, 7, 14, 28 and 60. On sample days, cows were quarter milked (i.e. samples were collected from individual glands) AM and PM, milk volumes were recorded and 100 ml sample retained. AM and PM quarter milk samples were pooled for laboratory analyses.

Blood and colostrum/milk samples were treated according to the format used for Example 1.

Sample Analysis

The ELISA assay for *C. albicans* was performed according to the format used for Example 1, with the exception that: *C. albicans* (5 mg/ml) was used for plate coating; second antibody used to identify class specificity was rabbit anti-bovine IgA (1:40K; Bethyl Laboratories, USA); enzyme conjugated antibody was goat anti-rabbit (1:12K; Dako, Denmark). The end point detection system was the same as in Example 1.

Figure 12:
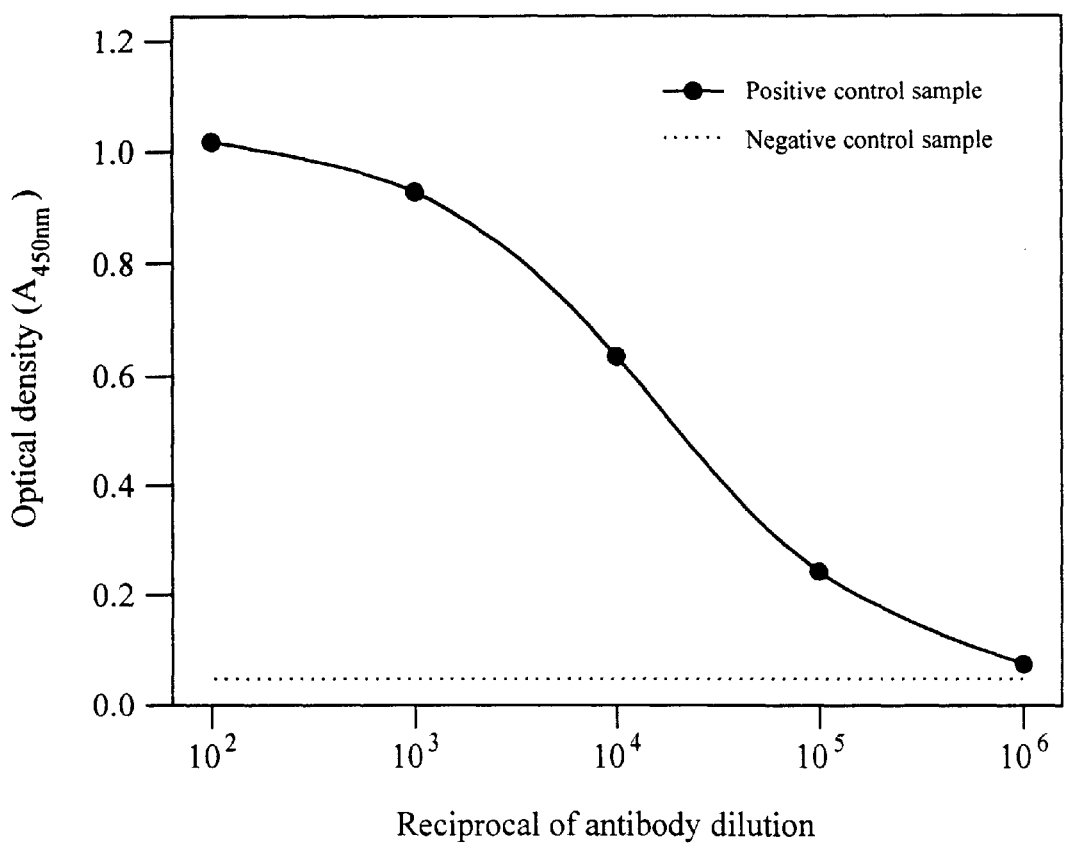
FIG. 12 shows a typical dilution curve for positive and negative control samples in the *C. albicans* IgA ELISA.

FIG. 12 shows a typical antibody dilution curve for the positive control sample.

Results

For Groups 1a, 1b and 1c, the anti-*C. albicans* IgA milk antibody titres were highest on Day 1 (parturition) with levels falling over the lactation period, as observed with the earlier sheep trials (Examples 1–4).

Two site versus three site immunisation

Figure 13:
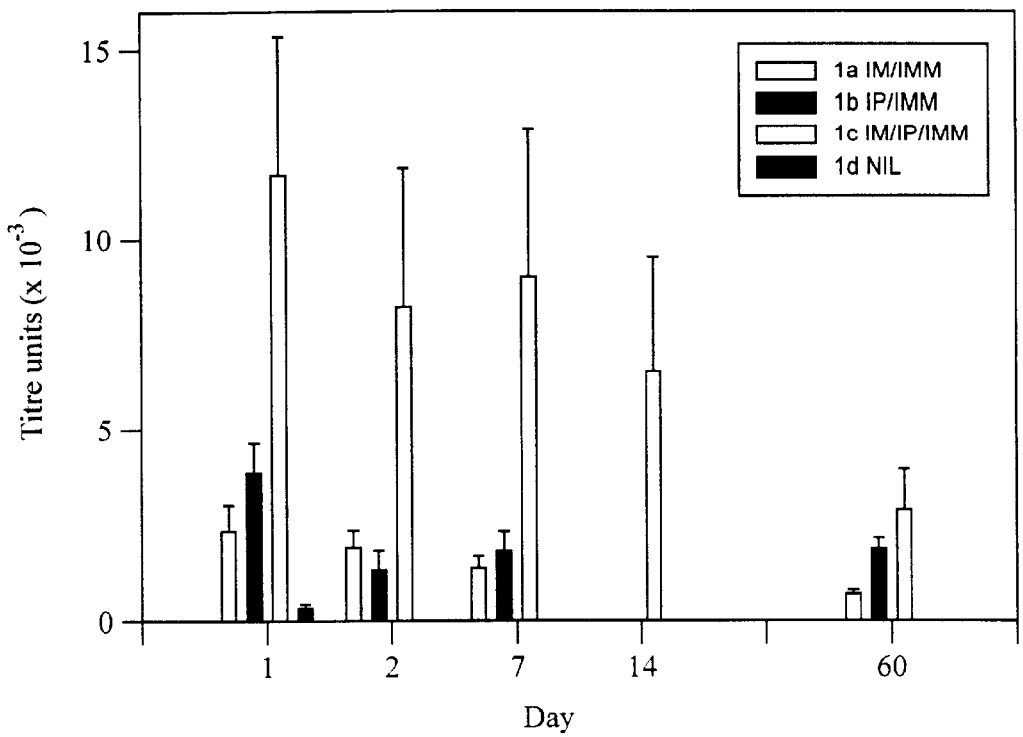
FIG. 13 shows the right (IMM immunogen in FIC) gland milk anti-*C. albicans* IgA antibody titre for all groups on Day 1, 2, 7, 14 and 60.

FIG. 13 shows the right (IMM immunogen in FIC) gland milk anti-*C. albicans* IgA antibody titres for all groups on Day 1, 2, 7, 14 and 60. Animals immunised at three sites (Group 1c; IM/IP/IMM) had a much higher response then animals immunised at two sites (Group 1a; IM/IMM and Group 1b; IP/IMM). The mean ±s.e.m. antibody titres were 11,700±3,700, 2,500±700 and 3,000±900, respectively. Group 1d (Control) had a very low antibody titre on Day 1 (titre of 200±70). The higher titres for animals immunised at three sites was maintained over the lactation period.

Freund's versus saline for IMM immunisations

FIG. 14 shows the milk anti-*C. albicans* IgA titre comparison of the left (aqueous IMM immunogen) and right (FIC IMM immunogen) glands in Group 1c over the lactation period. Glands immunised with immunogen emulsified in FIC gave a higher response than glands immunised with aqueous immunogen and this difference increased with time. On Day 1 the right gland titre was 11,700±3,700 compared to the left gland titre of 8,700±2,900. By Day 60, the left gland titre had declined to 590±200 while the right gland titre was 4 fold higher (2,300±800). This difference between left and right gland response was also apparent in the groups immunised at two sites (Group 1a and 1b).

Thus, in accordance with the present invention there is provided a process for the induction of IgA in a mammal, and the production of IgA in mammalian milk at levels higher than have previously been obtained or might have been anticipated from combining a third administration route for an antigen with known two route administration protocols. Alternatively, the present invention at least provides a method whereby the between animal variability in IgA antibody titre response can be reduced. It will be appreciated that these results represent an advantage where products containing IgA are sought for use in pharmaceutical, veterinary and cosmetic formulations as well as in nutritional and dietary supplements.

It will be further appreciated by those persons skilled in the art that the present description is provided by way of example only and that the scope of the invention is not limited thereto.

REFERENCES

1. Immune Response of Pregnant cows to Bovine Rotavirus Immunisation, Saif L. J. et al; American Journal of Veterinary Research (1984), 45: 1, 49–58.
2. Comparative Effect of Selected Adjuvants on the Response in the Bovine Mammary Gland to Staphylococcal and Streptococcal antigens, Opdebeeck, J. P. and Norcross, N. L; Veterinary Immunopathology (1984), 6: 341–351.
3. Novel Vaccination Strategies for the Control of Mucosal Infection, Husband, A. J; Vaccine (1993), 11: 2, 107–112.
4. Immunological Effector Mechanisms in Ruminants, D. L. Watson, I. G. Colditz, H. S. Gill; in Vaccines in Agriculture (1994), pp 21–36, eds Wood et al, CSIRO, Australia.
5. Responses of Antibody Titres to Intramammary Immunization with *Escherichia coli* J5 Bacterin; J. S. Hogan, K. L. Smith, P. Schoenberger, S. Romig and L. Thompson; J Dairy Sci. (1997) 80: 2398–2402.
6. Immune Mechanisms of the Ruminant Mammary Gland, R. F. Sheldrake; Australian Journal of Dairy Technology (1987), 42:1–2, 30–32.
7. The Effect of Intraperitoneal and Intramammary immunization of sheep on the numbers of antibody-containing cells in the mammary gland, and antibody titres in blood serum and mammary secretions; R. F. Sheldrake, A. J. Husband, D. L. Watson, A. W. Cripps; Immunology (1985), 56: 605–614.
8. Specific antibody-containing cells in the mammary gland of non-lactating sheep after intraperitoneal and intramammary immunisation; R. F. Sheldrake, A. J. Husband, D. L. Watson, Research in Veterinary Science (1985), 38: 312–316.
9. Vaccination against enteric Rota and Coronaviruses in cattle and pigs: enhancement of lactogenic immunity, C. F. Crouch; Vaccine (1985), 3: 284–291.
10. The mucosal immune system with particular reference to ruminant animals, A. K. Lascelles, K. J. Beh, T. K. Mukkur, D. L. Watson; in The Ruminant Immune System in Health and Disease (1986), pp 429–457, eds Morrison, Cambridge University Press, UK
11. Origin of antibody-containing cells in the ovine mammary gland following intraperitoneal and intramammary immunisation, R. F. Sheldrake, A. J. Husband, D. L. Watson; Research in Veterinary Science (1988), 45, 156–159.
12. IgA immune responses in the respiratory tract of pigs; R. F. Sheldrake; Research in Veterinary Science, (1990), 49, 98–103.
13. The Development of Vaccines to Protect Mucosal Surfaces; A. J. Husband, M. L. Dunkley, V. L. Clifton, in Health and Production for the 21st Century (1993), pp 82–88, ed Beh, CSIRO, Australia
14. Treatment of Infantile *E. coli* Gastroenteritis with Specific Bovine anti-*E. coli* Milk Immunoglobulins; C. Mietens, H. Keinhorst, H. Hilpert, H. Gerber, H. Amster, J. J. Pahud; Eur. J. Pediatr. (1979), 132:239–252.
15. Bovine Milk Antibodies in the Treatment of Enteric Infections and their ability to eliminate virulence factors from pathogenic *E. coli*; J. J. Pahud, H. Hilpert, K. Schwarz, H. Amster, M. Smiley; in Advances in Exp. Med & Biol.: The Ruminant Immune System (1981), pp 591–600, ed Butler, Plenum Press, NY
16. Use of Bovine Milk Concentrate Containing Antibody to Rotavirus to treat Rotavirus Gastroenteritis in Infants; H. Hilpert, H. Brussow, C. Mietens, J. Sidoti, L. Lerner, H. Werchau; Journal of Infectious Diseases (1987), 156: 1, 158–166.
17. Bovine Milk Immunogobulins for Passive Immunity to Infantile Rotavirus Gastroenteritis; H. Brussow, H. Hilpert, I. Walther, J. Sidoti, C. Mietens, P. Bachmann; Journal of Clinical Microbiology (1987), 25: 6, 982–986.
18. Antibodies: A Laboratory Manual (1988), p110–114; ed Harlan Cold SpringWater Laboratory, NY.
19. Review of Polyclonal Antibody Production Procedures, Hanly et al; ILAR Journal (1995), 37:3, 93–118.
20. Purification of Secretory IgA from Bovine Colostrum, Kanamaru et al; Agric. Biol. Chem(1982),46:16, 1531–1537.
21. A Method for Preparation of IgA from Bovine Mammary Secretions, Nielson, K; Can. J. Vet. Res (1986); 50: 227–231.
22. Ultrafiltration and Gel Filtration methods for separation of Immunoglobulins with secretory component from bovine milk, Kanamaru et al; Milchwissenschaft (1993), 48: 5, 247–251.
23. Antibodies from Milk for the prevention and Treatment of Diarrheal disease, Ruiz, L. P; in Indigenous Antimicrobial Agents of Milk—Recent Developments (1994), pp 108–121, International Dairy Federation, Brussels, Belguim.
24. Chronic Cryptosporidial Diarrhoea and Hyperimmune Cow Colostrum, Tzipori, Roberton, Cooper, White; Lancet (1987), II: 8554, 344–345.
25. Production of Hyperimmune Bovine Colostrum against Campylobacter Jejuni; Husu, Syvaoja, Ahola-Luttila, Kalsta, Sivela, Kosunen; Journal of Applied Bacteriology (1993), 74:5, 564–559.
26. Production and Preparation of Hyperimmune Bovine Colostrum for passive Immunotherapy of Cryptosporidiosis; Fayer, Tilley, Upton, Guidry, Thayer, Hildreth, Thomson; Journal of Protozoology (1991), 38:6, 38S-39S
27. Efficacy of Bovine Milk Immunoglobulin Concentrate in Preventing Illness after Shigella Flexneri Challenge; Tacket, Binion, Bostwick, Losonsky, Roy, Edelman; American Journal of Tropical Medicine and Hygiene, (1992) 47:3, 276–283.
28. Protection of Gnotobiotic rats against dental caries by passive immunization with Bovine Milk Antibodies to Streptococcus mutans; Michalek, Gregory, Harmon, Katz, Richardson, Hilton, Filler, McGhee; Infection and Immunity (1987), 55: 10, 2341–2347.
29. Cessation of Cryptosporidium-associated Diarrhea in an acquired Immunodeficiency Syndrome Patient after Treatment with Hyperimmune Bovine Colostrum; Ungar, Ward, Fayer, Quinn; Gastroenterology New York (1990), 90: 2, 486–489.
30. Bovine Colostrum Immunoglobulin Concentrate for Cyrptosporidiosis in AIDS; Heaton; in Archives of Disease in Childhood (1994), 70: 4, 356–357.

All articles and patents referenced here and in the disclosure are incorporated by reference.

What is claimed is:

1. A process for the production for immunoglobulin A (IgA) in the milk of a ruminant comprising:
   (a) actively immunizing a pregnant ruminant with an antigen by any two routes of administration selected from the group consisting of intra mammary (IMM) intra peritoneal (IP) and intramuscular (TM); and
   (b) actively immunizing said ruminant with an antigen by a third administration route selected from the group consisting of intra mammary (IMM), intra peritoneal (IP) and intramuscular (IM); with the proviso that all three administration routes are different; and
   wherein a higher IgA titre is produced as compared to an IgA titre produced by conducting step (a) alone.

2. The process according to claim 1 wherein step (a) the two routes of administration selected are IP and IM and instep (b) the third route of administration is IMM.

3. The process according to claim 1 wherein the two active immunizations of step (a) are effected by a sequence selected from sequentially, set apart in time, and concurrently.

4. The process according to claim 3 wherein the two active immunizations of step (a) are effected concurrently.

5. The process according to claim 1 wherein steps (a) and (b) are effected by a sequence selected from sequentially, set apart in time and concurrently.

6. The process according to claim 1 wherein steps (a) and (b) are each repeated at least once prior to parturition.

7. The process according to claim 1 wherein step (a) is repeated twice, prior to parturition.

8. The process according to claim 7 wherein each step (a) is effected at an interval in the range 2 to 8 weeks.

9. The process according to claim 8 wherein each step (a) is effected at an interval in the range 2 to 4 weeks.

10. The process according to claim 6 wherein step (a) is effected 6 to 14 weeks prior to parturition, a first repeat step (a) is effected at 2 to 10 weeks prior to parturition, and the last step (a) is effected at 1 to 4 weeks prior to parturition.

11. The process according to claim 10 wherein step (a) is effected 8 to 12 weeks prior to parturition, the first repeat step (a) is effected at 4 to 8 weeks prior to parturition, and the final step (a) is effected as 1 to 4 weeks prior to parturition.

12. The process according to claim 11 wherein step (a) is effected 8 weeks prior to parturition, first repeat step (a) is effected at 4 weeks prior to parturition, and the final step (a) is effected at 1 week prior to parturition.

13. The process according to claim 6 wherein step (b) is repeated once prior to parturition.

14. The process according to claim 6 wherein the repetitions of step (b) are effected at 1 to 6 week intervals.

15. The process according to claim 14 wherein the repetition is at 2 week intervals.

16. The process according to claim 13 wherein a first step (b) is effected 3 to 12 weeks prior to parturition, and a second step (b) is effected at 1 to 10 weeks prior to parturition.

17. The process according to claim 16 wherein the first step (b) is effected 4 to 8 weeks prior to parturition and the repeat step (b) is effected 2 to 4 weeks prior to parturition.

18. The process according to claim 17 wherein the first step (b) is effected 4 weeks prior to parturition and the repeat step (b) is effected at 2 weeks prior to parturition.

19. The process according to claim 1 wherein the antigen comprises at least one of the group of bacteria, yeasts, viruses, mycoplasmas, proteins, haptens, animal tissue extracts, plant tissue extracts, spermatozoa, fungi, pollens, dust and a complex of antigens.

20. The process according to claim 19 wherein the antigen is a yeast antigen.

21. The process according to claim 20 wherein the yeast is *Candida albicans*.

22. The process according to claim 19 wherein the antigen is a protein antigen.

23. The process according to claim 1 wherein the antigen is formulated as a suspension.

24. The process according to claim 1 wherein the antigen is administered together with a compound selected from an acceptable carrier, a diluent, a buffer, an adjuvant and a combination thereof.

25. The process according to claim 23 wherein the antigen is administered together with an adjuvant.

26. The process according to claim 24 wherein the adjuvant is selected from the group: Freund's complete adjuvant (FCA); Freund's incomplete adjuvant (FIC); cholera toxin B subunit; aluminum hydroxide.

27. The process according to claim 24 wherein the adjuvant is *Bordetella pertussis,* a muramyl dipeptide, a cytokine, or a saponin.

28. The process according to claim 24 wherein the adjuvant is Freund's incomplete adjuvant.

29. The process according to claim 1 wherein the antigen is administered together with an antibiotic.

30. The process according to claim 1 wherein the antigen administered in each immunizing process, and at each site, is the same or different.

31. The process according to claim 24 wherein the antigen administered in each immunizing process, and at each site, is the same.

32. The process according to claim 1 wherein the ruminant immunized is selected from the group consisting of cows, goats and sheep.

33. The process according to claim 32 wherein the ruminant is a dairy cow.

* * * * *